United States Patent
Kurioka et al.

(10) Patent No.: US 10,731,198 B2
(45) Date of Patent: Aug. 4, 2020

(54) SENSOR, DETECTION METHOD, DETECTION SYSTEM, AND DETECTION DEVICE

(71) Applicants: KYOCERA Corporation, Kyoto-shi, Kyoto (JP); KYUSHU UNIVERSITY, NATIONAL UNIVERSITY CORPORATION, Fukuoka-shi, Fukuoka (JP)

(72) Inventors: Hideharu Kurioka, Kizugawa (JP); Shinsuke Sando, Fukuoka (JP)

(73) Assignees: KYOCERA Corporation, Kyoto (JP); Kyushu University, National University Corporation, Fukuoka (JP)

( * ) Notice: Subject to any disclaimer, the term of this patent is extended or adjusted under 35 U.S.C. 154(b) by 146 days.

(21) Appl. No.: 14/410,042

(22) PCT Filed: Jun. 26, 2013

(86) PCT No.: PCT/JP2013/067569
§ 371 (c)(1),
(2) Date: Mar. 24, 2015

(87) PCT Pub. No.: WO2014/003075
PCT Pub. Date: Jan. 3, 2014

(65) Prior Publication Data
US 2015/0232912 A1     Aug. 20, 2015

(30) Foreign Application Priority Data

Jun. 26, 2012 (JP) ................ 2012-143304

(51) Int. Cl.
*C12Q 1/26*       (2006.01)
*G01N 33/52*    (2006.01)
(Continued)

(52) U.S. Cl.
CPC ........... *C12Q 1/26* (2013.01); *C12M 41/34* (2013.01); *C12Q 1/28* (2013.01); *G01N 29/036* (2013.01);
(Continued)

(58) Field of Classification Search
None
See application file for complete search history.

(56) References Cited

U.S. PATENT DOCUMENTS

| 5,503,770 A | 4/1996 | James et al. |
| 6,462,179 B1 | 10/2002 | Stolowitz et al. |

(Continued)

FOREIGN PATENT DOCUMENTS

| JP | 08-053467 A | 2/1996 |
| JP | 2005-502873 A | 1/2005 |

(Continued)

OTHER PUBLICATIONS

Ananthi et al., Materials Letters 65: 3563-3565 (2011).*
(Continued)

*Primary Examiner* — Erin M. Bowers
(74) *Attorney, Agent, or Firm* — Procopio Cory Hargreaves and Savitch LLP

(57) ABSTRACT

A sensor determines whether a specimen includes a first substance. In an exemplary embodiment, the sensor includes a base. In an exemplary embodiment, the sensor is configured to determine whether the specimen includes the first substance and further includes, on the base, a detection unit on which a second substance is immobilized. The second substance includes a bond that is cleft by the reaction with hydrogen peroxide. In an exemplary embodiment, the specimen that is brought in contact with an enzyme that generates the hydrogen peroxide by the reaction with the first substance is introduced to the detection unit in the sensor (Continued)

configured to determine whether the specimen includes the first substance.

16 Claims, 12 Drawing Sheets

(51) Int. Cl.
   *C12Q 1/28* (2006.01)
   *C12M 1/34* (2006.01)
   *G01N 29/036* (2006.01)
   *G01N 29/22* (2006.01)
   *G01N 33/84* (2006.01)

(52) U.S. Cl.
   CPC ........... *G01N 29/223* (2013.01); *G01N 33/52* (2013.01); *G01N 33/84* (2013.01)

(56) References Cited

U.S. PATENT DOCUMENTS

| | | |
|---|---|---|
| 2002/0090734 A1 | 7/2002 | Daniloff et al. |
| 2002/0127626 A1 | 9/2002 | Daniloff et al. |
| 2003/0068655 A1 | 4/2003 | Bottomley et al. |
| 2003/0082663 A1 | 5/2003 | Daniloff et al. |
| 2004/0029108 A1 | 2/2004 | Bottomley et al. |
| 2004/0166539 A1 | 8/2004 | Akhavan-Tafti et al. |
| 2004/0171098 A1* | 9/2004 | Akhavan-Tafti ........ C07F 5/025 435/25 |
| 2005/0043275 A1 | 2/2005 | Daniloff et al. |
| 2006/0024813 A1* | 2/2006 | Warthoe ................. B82Y 15/00 435/287.1 |
| 2008/0261318 A1 | 10/2008 | Akhavan-Tafti et al. |
| 2010/0055800 A1 | 3/2010 | Akhavan-Tafti et al. |

FOREIGN PATENT DOCUMENTS

| | | |
|---|---|---|
| JP | 2006-104140 A | 4/2006 |
| JP | 2007-538236 A | 12/2007 |

OTHER PUBLICATIONS

Rishpon et al., Electroanalysis 6: 17-21 (1994).*
Ananthi A. et al., A novel potentiometric hydrogen peroxide sensor based on pKa changes of vinylphenylboronic acid membranes, Materials Letters, 2011, vol. 65, p. 3563-3565.
Hiroshi Muramatsu, "Atsuden Soshi o Mochiiru Biosensing", Iden, 1989, vol. 43, No. 1, pp. 25 to 29.
Jun Kondoh et al., "Enzyme Biosensor Based on Surface Acoustic Wave Device", the Transactions of the Institute of Electronics, Information and Communication Engineers C-I, 1995, vol. 78, No. 11, pp. 599 to 604.
International Search Report dated Sep. 17, 2013, issued for International Application No. PCT/JP2013/067569.
Office Action dated Jun. 27, 2017 issued in counterpart Japanese Application No. 2016-130139.
Ananthi et al., A novel potentiometric hydrogen peroxide sensor based on pKa changes of vinylphenylboronic acid membranes, Nanoscale Electrocatalysis and Sensor Research Group, Electrodics and Electrocatalysis Division, CSIR-Central Electrochemical Research Institute, Karaikudi-630006, India, Materials Letters 65 (2011), p. 3563-3565, www.elsevier.com/locate/matlet.
Smirnova et al, Development of a Micro-Potentiometric Sensor for the Microchip Analysis of Alkali Ions, The Japan Society for Analytical Chemistry, 2009, Analytical Sciences, Dec. 2009, vol. 25, p. 1397-1401.

* cited by examiner

100

SENSOR, DETECTION METHOD, DETECTION SYSTEM, AND DETECTION DEVICE

CROSS-REFERENCE TO RELATED APPLICATIONS

This application is national stage application of International Application No. PCT/JP2013/067569, filed on Jun. 23, 2013, which designates the United States, incorporated herein by reference, and which claims the benefit of priority from Japanese Patent Application No. 2012-143304, filed on Jun. 26, 2012, the entire contents of which are incorporated herein by reference.

FIELD

The present invention relates to a sensor, a detection method, a detection system, and a detection apparatus.

BACKGROUND

There is a technique for detecting hydrogen peroxide with a signalling compound that generates a species that can be detected by the reaction with the hydrogen peroxide. For example, the technique for detecting hydrogen peroxide detects a hydrogen peroxide source by detecting the color, absorbance, fluorescence, chemiluminescence, or bioluminescence caused by the species generated by the reaction with the hydrogen peroxide.

There is a detection method that detects the variations in state of the surface of a base. For example, there is a sensor that measures a characteristic or ingredient of a specimen with a surface acoustic wave. Alternatively, there is, for example, a Surface Plasmon Resonance (SPR) measurement apparatus. Note that there is also a technique for measuring the glucose concentration in solution.

CITATION LIST

Patent Literature

Patent Literature 1: Japanese National Publication of International Patent Application No. 2005-530130
Patent Literature 2: Japanese Patent Application Laid-open No. 2006-104140
Patent Literature 3: Japanese National Publication of International Patent Application No. 2006-520465
Patent Literature 4: Japanese Patent Application Laid-open No. 8-053467
Patent Literature 5: U.S. Pat. No. 6,462,179

SUMMARY

Technical Problem

Unfortunately, the techniques described above fail to readily detect a hydrogen peroxide source.

In light of the foregoing, an objective of the disclosed technique is to provide a sensor, detection method, detection system, and detection apparatus that can readily detect a hydrogen peroxide source.

Solution to Problem

A sensor, a detection method, a detection system and a detection apparatus, as disclosed according to one aspect, includes a sensor configured to determine whether a specimen includes a first substance, and the sensor includes: a base; and a detection unit including a second substance including a bond that is cleft by a reaction with hydrogen peroxide is immobilized on the base, wherein the specimen that is brought in contact with an enzyme that generates the hydrogen peroxide by the reaction with the first substance, and the specimen is introduced to the detection unit.

Advantageous Effects of Invention

An aspect of the disclosed sensor, detection method, detection system, and detection apparatus has the effect that allows for easy detection of a hydrogen peroxide source.

DESCRIPTION OF EMBODIMENTS

Figure 1:
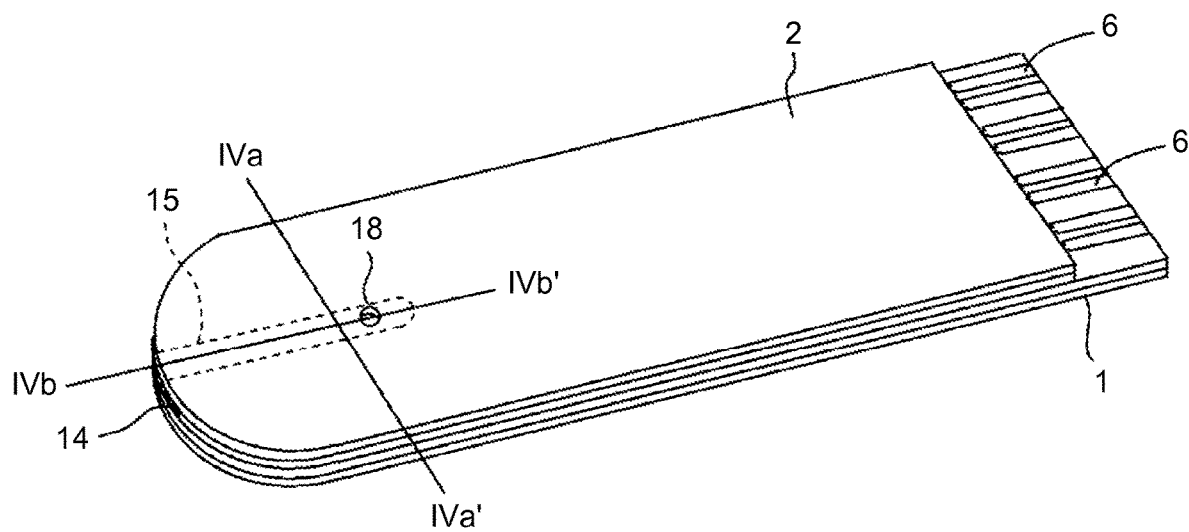
FIG. 1 is a perspective view of a sensor according to an embodiment of the present invention.
Figure 1:
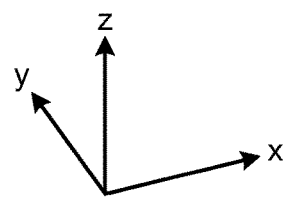

The embodiments of the disclosed sensor, detection method, detection system, and detection apparatus will be described in detail with appropriate reference to the appended drawings. As described below, the disclosed sensor, detection method, detection system, and detection apparatus are a sensor configured to determine whether a specimen includes a first substance. The sensor includes a detection unit on the surface of its base. A second substance is immobilized on the detection unit. The second substance includes a bond that is cleft by the reaction with hydrogen peroxide. A specimen is brought into contact with an enzyme that generates the hydrogen peroxide by the reaction with the first substance and then is introduced into the detection unit. In other words, a specimen is brought into contact with an enzyme that generates hydrogen peroxide by the reaction with the first substance. The specimen is brought into contact with the detection unit of a sensor 100. A second substance 200 is immobilized on the detection unit. The second substance 200 includes a bond that is cleft by the reaction with hydrogen peroxide in a bonding portion 210. The variations in the state of the detection unit on the base in contact with the specimen are detected, and thus, it is detected whether the specimen includes the first substance or not. As a result, a hydrogen peroxide source can be detected easily.

Note that the first substance to be detected is also referred to as a "target substance" hereinafter. A range of numerical values indicated with "to" includes the upper limit and lower limit unless otherwise noted. For example, the range of numerical values "300 to 500" indicates that the lower limit is "equal to or higher than 300" and the upper limit is "equal to or lower than 500" unless otherwise noted.

[Configuration of Sensor]

The disclosed sensor is used for a detection method that detects the variations in the state of the surface of the base. The disclosed sensor is, for example, a measurement cell used for measurement with a Surface Plasmon Resonance (SPR) apparatus, a Surface Acoustic Wave (SAW) sensor, or a Quartz Crystal Microbalance (QCM) quartz sensor. The disclosed sensor is preferably an SAW sensor. Implementing the sensor as an SAW sensor can downsize and easily implement the sensor.

An SAW sensor used as the disclosed sensor will be described in detail hereinafter as an exemplary configuration of the disclosed sensor. As described in detail below, the sensor 100 that is an SAW sensor includes a first cover member in an exemplary embodiment. A base is placed on the upper surface of the first cover member. The sensor 100 further includes a second cover member joined to the first cover member. At least one of the first cover member and the second cover member includes an inlet into which the specimen flows and a groove extending from the inlet at least to the surface of the base in the sensor 100. For example, the first cover member includes a concave portion on its upper surface in the sensor 100, which is an SAW sensor, as an exemplary embodiment. The base is accommodated in the concave portion. The second cover member includes the groove.

The sensor 100, which is an SAW sensor, includes a first InterDigital Transducer (IDT) electrode in an exemplary embodiment. The first IDT electrode is placed on the surface of the base to generate an acoustic wave that propagates toward the detection unit to be described in detail below. The sensor 100 further includes a second IDT electrode placed on the surface of the base to receive the acoustic wave that has passed through the detection unit 13. The sensor 100 further includes a first join member joined to the upper surface of the base to provide a first oscillation space on the first IDT electrode. The first IDT electrode is sealed in the first oscillation space with the first join member. The sensor 100 further includes a second join member joined to the upper surface of the base to provide a second oscillation space on the second IDT electrode. The second IDT electrode is sealed in the second oscillation space with the second join member. In other words, the sensor 100 includes the first join member joined to the upper surface of the base and including the first oscillation space sealed between the first join member and the upper surface of the base. The sensor 100 includes the second join member joined to the upper surface of the base and including the second oscillation space sealed between the second join member and the upper surface of the base. The first oscillation space is placed on the first IDT electrode, and the second oscillation space is placed on the second IDT electrode in the sensor 100.

An exemplary configuration of the sensor 100, which is an SAW sensor, will be described in detail with appropriate reference to the appended drawings. Note that the same components to be described below in each drawing are denoted with the same reference signs. The size of each component and the distance between the components are sometimes different from the actual size and distance because of being schematically illustrated. The upper side or lower side of the sensor 100 may face any direction. However, an orthogonal coordinate system x, y, and z is defined hereinafter while the positive side of the z direction is the upper side and the words such as an upper surface and lower surface are used for descriptive purposes.

The sensor 100 mainly includes a first cover member 1, a second cover member 2, and a detection element 3. The first cover member 1 includes a first base 1a, and a second base 1b stacked on the first base 1a. The second cover member 2 includes a third base 2a stacked on the second base 1b, and a fourth base 2b stacked on the third base 2a. The detection element 3, which is a surface acoustic wave device, mainly includes a base 10, a first IDT electrode 11, a second IDT electrode 12, and a detection unit 13.

The first cover member 1 and the second cover member 2 are stuck to each other. The detection element 3 is accommodated in the inside of the stuck first cover member 1 and second cover member 2. As illustrated in the cross-sectional views of FIGS. 4A and 4B, the first cover member 1 includes a concave portion 5 on its upper surface so that the detection element 3 is placed in the concave portion 5.

As illustrated in FIG. 1, the second cover member 2 includes an inlet 14 that is an entrance for the specimen at a first longitudinal (x-direction) end portion, and a groove 15 extending from the inlet 14 to the portion just above the detection element 3. Note that FIG. 1 illustrates the groove 15 with a dashed line to show the position of the groove 15.

Figure 2:
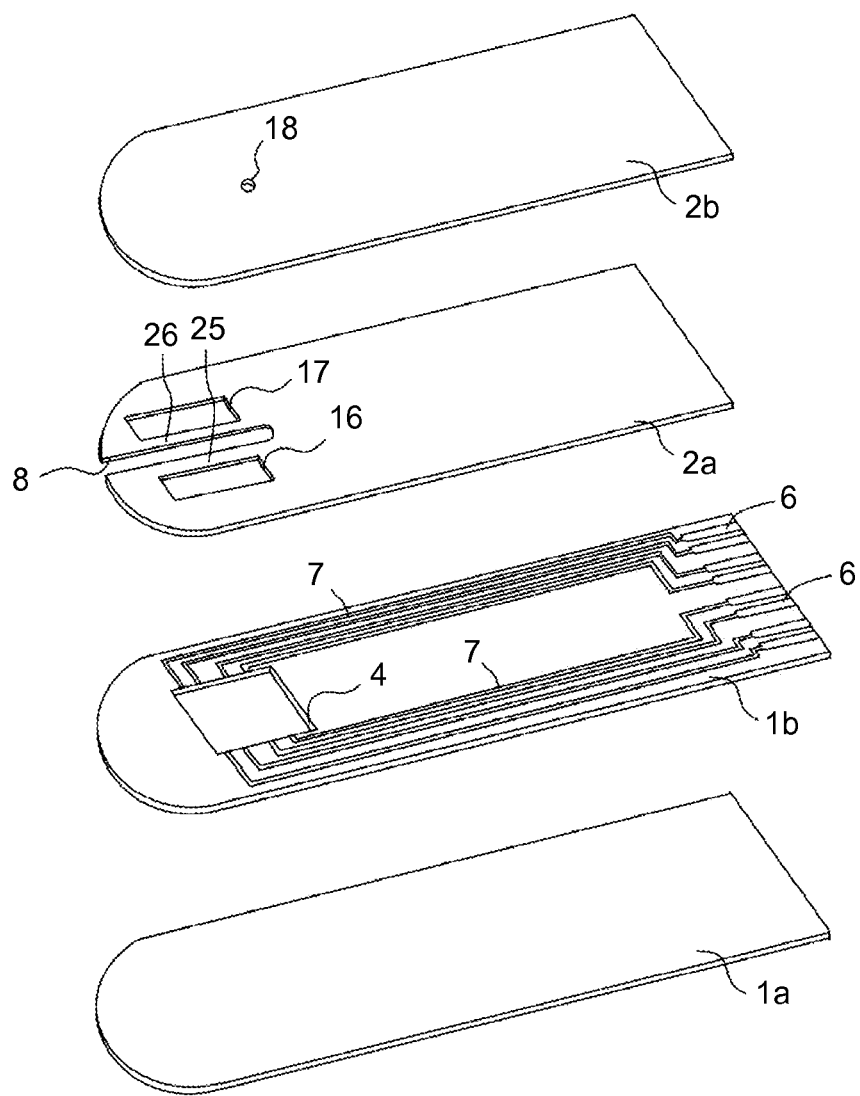
FIG. 2 is an exploded perspective view of a first cover member and a second cover member.

FIG. 2 is an exploded perspective view of the first cover member 1 and the second cover member 2.

The first base 1a included in the first cover member 1 has a flat board shape and a thickness, for example, of 0.1 to 0.5 mm. The flat surface of the first base 1a has an approximate rectangular shape. However, a first longitudinal end of the flat surface is an arc protruding outward. The first base has a length, for example, of 1 to 5 cm in the x direction and, for example, of 1 to 3 cm in the y direction.

The second base 1b is stuck to the upper surface of the first base 1a. The second base 1b is a flat frame that is a flat board on which a concave portion forming through-hole 4 is provided. The second base 1b is, for example, 0.1 to 0.5 mm in thickness. As viewed in planar view, the second base 1b has almost the same external shape as the first base 1a, and almost the same lengths in the x and y directions as the first base 1a.

Joining the second base 1b on which the concave portion forming through-hole 4 is provided to the first base 1a having a flat board shape forms the concave portion 5 on the first cover member 1. In other words, the upper surface of the first base 1a, which is placed inside the concave portion forming through-hole 4, is the bottom surface of the concave portion 5. The internal wall of the concave portion forming through-hole 4 is the internal wall of the concave portion 5.

Terminals 6 and wires 7 drawn from the terminals 6 to the concave portion forming through-hole 4 are formed on the upper surface of the second base 1*b*. The terminals 6 are formed on a second end portion of the upper surface of the second base 1*b* in the x direction. The portion on which the terminals 6 are formed is the portion to actually be inserted when the sensor 100 is inserted into an external measurement instrument (not illustrated). The sensor is to electrically be connected to the external measurement instrument through the terminals 6. The terminals 6 and the detection element 3 are electrically connected, for example, through the wires 7. This inputs a signal from the external measurement instrument through the terminal 6 to the sensor 100, and outputs a signal from the sensor 100 through the terminal 6 to the external measurement instrument.

The second cover member 2 is joined to the upper surface of the first cover member 1 including the first base 1*a* and the second base 1*b*. The second cover member 2 includes the third base 2*a* and the fourth base 2*b*.

The third base 2*a* is stuck to the upper surface of the second base 1*b*. The third base 2*a* has a flat board shape and a thickness, for example, of 0.1 to 0.5 mm. The flat surface of the third base 2*a* has an approximate rectangular shape. However, a first longitudinal end is an arc protruding outward, similarly to the first base 1*a* and the second base 1*b*. The length of the third base 2*a* in the x direction is slightly shorter than the length of the second base 1*b* in the x direction such that the terminals 6 formed on the second base 1*b* are exposed. The third base 2*a* is, for example, 0.8 cm to 4.8 cm in the x direction. The third base 2*a* has a length, for example, of 1 to 3 cm in the y direction, similarly to the first base 1*a* and the second base 1*b*.

The third base 2*a* has a length, for example, of 1 to 3 cm in the y direction, similarly to the first base 1*a* and the second base 1*b*.

A notch 8 is formed on the third base 2*a*. The notch 8 is formed by notching the third base 2*a* from the top of the first end that is an arc toward the second end in the x direction. The notch 8 is used to form the groove 15. A first through-hole 16 and a second through-hole 17 that penetrate the third base 2*a* in the thickness direction are formed on both sides of the notch 8 in the third base 2*a* such that the connections of the detection element 3 and the wires 7 are placed at the insides of the first through-hole 16 and second through-hole 17 when the third base 2*a* is stacked on the second base 1*b*. The portion between the first through-hole 16 and the notch 8 in the third base 2*a* is a first partition 25 configured to separate the groove 15 and the space formed with the first through-hole 16. The portion between the second through-hole 17 and the notch 8 in the third base 2*a* is a second partition 26 configured to separate the groove 15 and the space formed with the second through-hole 17.

The fourth base 2*b* is stuck to the upper surface of the third base 2*a*. The fourth base 2*b* has a flat board shape and has a thickness, for example, of 0.1 mm to 0.5 mm. As viewed in planar view, the fourth base 2*b* has almost the same external shape as the third base 2*a*, and almost the same lengths in the x and y directions as the third base 2*a*. Joining the fourth base 2*b* to the third base 2*a* in which the notch 8 is formed forms the groove 15 on the lower surface of the second cover member 2. In other words, the lower surface of the fourth base 2*b* placed in the notch 8 is the bottom surface of the groove 15. The internal wall of the notch 8 is the internal wall of the groove 15. The groove 15 extends from the inlet 14 at least to the region just above the detection unit 13, and has a cross-sectional surface, for example, having a rectangular shape.

A third through-hole 18 is formed on the fourth base 2*b* while penetrating the fourth base 2*b* in the thickness direction. The third through-hole 18 is placed on the end portion of the notch 8 when the fourth base 2*b* is stacked on the third base 2*a*. Thus the end portion of the groove 15 is connected to the third through-hole 18. The third through-hole 18 discharges, for example, the air in the groove 15 to the outside.

The first base 1*a*, the second base 1*b*, the third base 2*a*, and the fourth base 2*b* are each made, for example, of paper, plastic, celluloid, or ceramics. All of the bases may be made of the same material. Forming all of the bases with the same material enables the bases to have almost the same coefficients of thermal expansion. This can prevent the deformation caused by the difference among the coefficients of thermal expansion of the bases. A biomaterial is sometimes applied to the detection unit 13. Some of the biomaterials easily alter the qualities due to an external light such as ultraviolet rays. In such a case, an opaque material having light blocking effect may be used as the material of the first cover member 1 and the second cover member 2. On the other hand, if the quality of the detection unit 13 hardly alters due to the light outside the detection unit 13, the second cover member 2 on which the groove 15 is formed may be formed with a nearly transparent material. In such a case, the specimen flowing through the flow channel can visually be checked.

Figure 5:
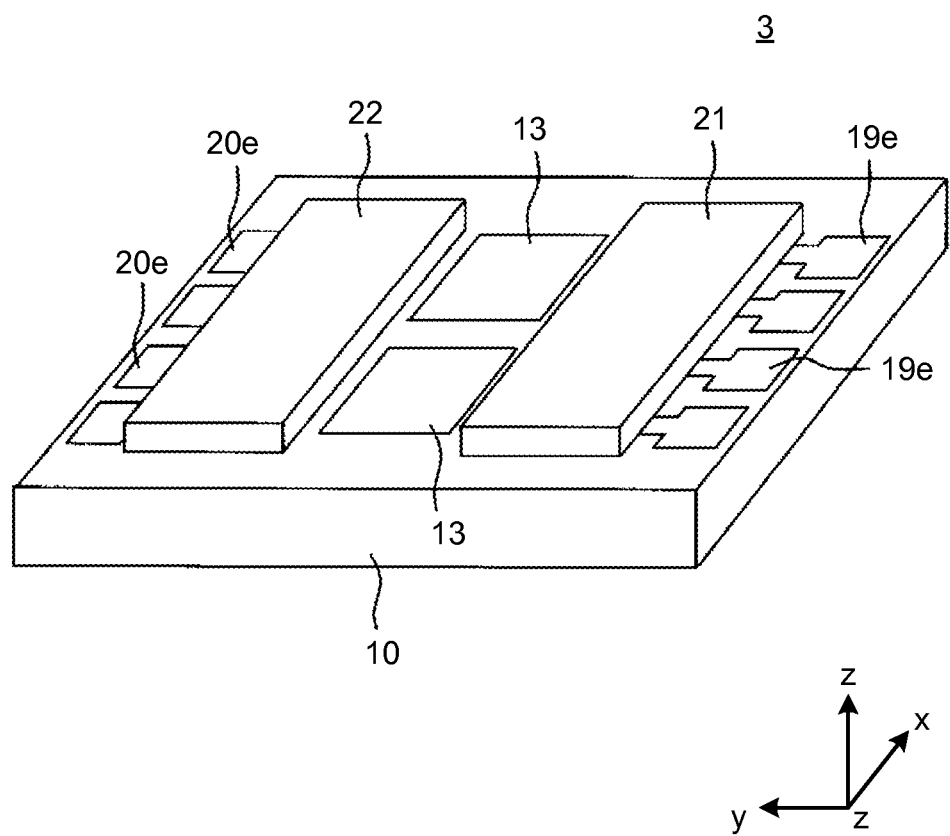
FIG. 5 is a perspective view of a detection element used in the sensor illustrated in FIG. 1.
Figure 6:
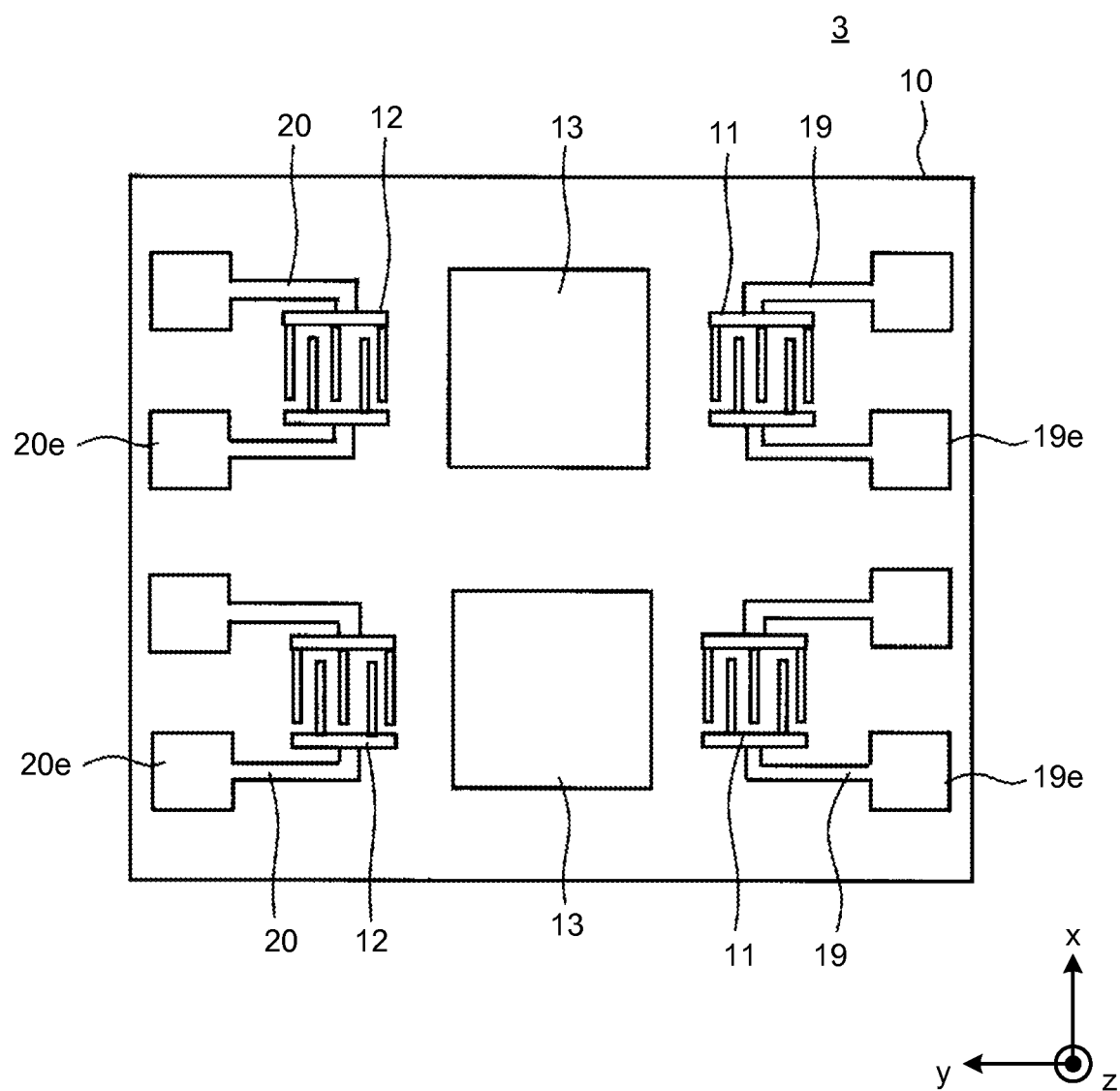
FIG. 6 is a plan view of the detection element illustrated in FIG. 5 from which the first join member and the second join member are removed.

Next, the detection element 3 will be described. FIG. 5 is a perspective view of the detection element 3. FIG. 6 is a plan view of the detection element 3 from which a first join member 21 and a second join member 22 are removed.

The detection element 3 includes the base 10, and the detection unit 13, the first IDT electrode 11, the second IDT electrode 12, the first connecting electrodes 19, and the second connecting electrodes 20 that are placed on the upper surface of the base 10.

The base 10 is a single-crystalline base made, for example, of piezoelectric single crystals such as lithium tantalate ($LiTaO_3$) single crystals, lithium niobate ($LiNbO_3$) single crystals, or crystal. The shape of the flat surface of the base 10 and each dimension may appropriately be set. For example, the base 10 has a thickness of 0.3 mm to 1.0 mm.

As illustrated in FIG. 6, the first IDT electrode 11 includes a pair of comb electrodes. Each of the comb electrodes includes a bus bar facing the bus bar of the opposite comb electrode and a plurality of electrode fingers extending from the bus bar to the opposite bus bar. The pair of comb electrodes is placed such that the electrode fingers mesh with each other. The second IDT electrode 12 has the same configuration as the first IDT electrode 11. The first IDT electrode 11 and the second IDT electrode 12 are each a transversal IDT electrode.

Using the number of the electrode fingers of the first IDT electrode 11 and second IDT electrode 12, the distance between the adjacent electrode fingers, the intersectional width between the electrode fingers as parameters can design the frequency characteristic. The SAW excited with the IDT electrodes is, for example, a Rayleigh wave, a Love wave, or a Leaky wave. Note that the first IDT electrode 11 may be provided with an elastic member used to prevent the reflection of the SAW at an outer region in the direction in which the SAW propagates. The frequency of the SAW may be set in a range, for example, from several megahertz (MHz) to several gigahertz (GHz). Especially, setting the range from hundreds MHz to two GHz is practical, and can downsize the base 10 and thus can implement a downsized SAW sensor.

The first IDT electrode 11 is configured to generate a predetermined Surface Acoustic Wave (SAW). The second IDT electrode 12 is configured to receive the SAW generated in the first IDT electrode 11. The first IDT electrode 11 and the second IDT electrode 12 are placed on a straight line such that the second IDT electrode 12 can receive the SAW generated in the first IDT electrode 11. Using the number of the electrode fingers of the first IDT electrode 11 and second IDT electrode 12, the distance between the adjacent electrode fingers, and the intersectional width between the electrode fingers as a parameter can design the frequency characteristic. Waves with various oscillation modes exist as the SAW excited with the IDT electrodes. For example, the oscillation mode of a shear wave referred to as an SH wave is used in the detection element 3.

The first IDT electrode 11 and second IDT electrode 12 may be provided with an elastic member used to prevent the reflection of the SAW at an outer region in the direction in which the SAW propagates (the y direction). The frequency of the SAW may be set in a range, for example, from several megahertz (MHz) to several gigahertz (GHz). In particular, setting in the range from hundreds MHz to two GHz is practical, and can downsize the detection element 3 and thus can implement a downsized sensor 100.

The first IDT electrodes 11 are connected to the first connecting electrodes 19. Each of the first connecting electrodes 19 is drawn from the first IDT electrode 11 to the side opposite to the detection unit 13. The end portion 19e of the first connecting electrode 19 is electrically connected to the wire 7 provided on the first cover member 1. The second IDT electrodes 12 are connected to the second connecting electrodes 20. Each of the second connecting electrodes 20 is drawn from the second IDT electrode 12 to the side opposite to the detection unit 13. The end portion 20e of the second connecting electrode 20 is electrically connected to the wire 7.

The first IDT electrodes 11, the second IDT electrodes 12, the first connecting electrodes 19, and the second connecting electrodes 20 are made, for example, of aluminum or an alloy of aluminum and copper. The electrodes may have a multi-layer structure. The multi-layer structure has, for example, a first layer made of titanium or chrome, and a second layer made of aluminum or an aluminum alloy.

The first IDT electrodes 11 and the second IDT electrodes 12 are covered with a protection film (Not illustrated). The protection film contributes, for example, to the prevention of oxidation of the first IDT electrodes 11 and the second IDT electrodes 12. The protection film is made, for example, of silicon oxide, aluminum oxide, zinc oxide, titanium oxide, silicon nitride, or silicon. The protection film has a thickness, for example, of about 1/10 of the thickness of the first IDT electrode 11 and second IDT electrode 12 (10 to 30 nm). The protection film may be formed on the whole upper surface of the base 10 while exposing the end portions 19e of the first connecting electrodes 19 and the end portions 20e of the second connecting electrodes 20.

The detection units 13 are provided between the first IDT electrodes 11 and the second IDT electrodes 12. Each of the detection units 13 includes a metal film. The detection unit 13 further includes a second substance 200 on the surface of the metal film. The second substance 200 includes a bonding portion 210 of which bond is cleft by the reaction with hydrogen peroxide. The detection unit 13 will be described below.

If the first IDT electrodes 11, the second IDT electrodes 12, and the detection unit 13 that are placed in the y direction are viewed as a set, the sensor 100 is provided with two sets of them. To one of the two detection units 13, a substance including the bonding portion 210 of which bond is cleft by the reaction with hydrogen peroxide may not be immobilized such that one of the detection units 13 may be used as a reference.

The first IDT electrodes 11 are covered with the first join member 21 as illustrated in FIG. 5. The first join member 21 is placed on the upper surface of the base 10 and has a hollow therein. The hollow of the first join member 21 placed on the upper surface of the base 10 is a first oscillation space 23. The first IDT electrode 11 is sealed in the first oscillation space 23. This can separate the first IDT electrode 11 from the ambient air and the specimen and thus can protect the first IDT electrode 11. Securing the first oscillation space 23 can prevent the deterioration of the characteristic of the SAW excited in the first IDT electrode 11.

Figure 4A:
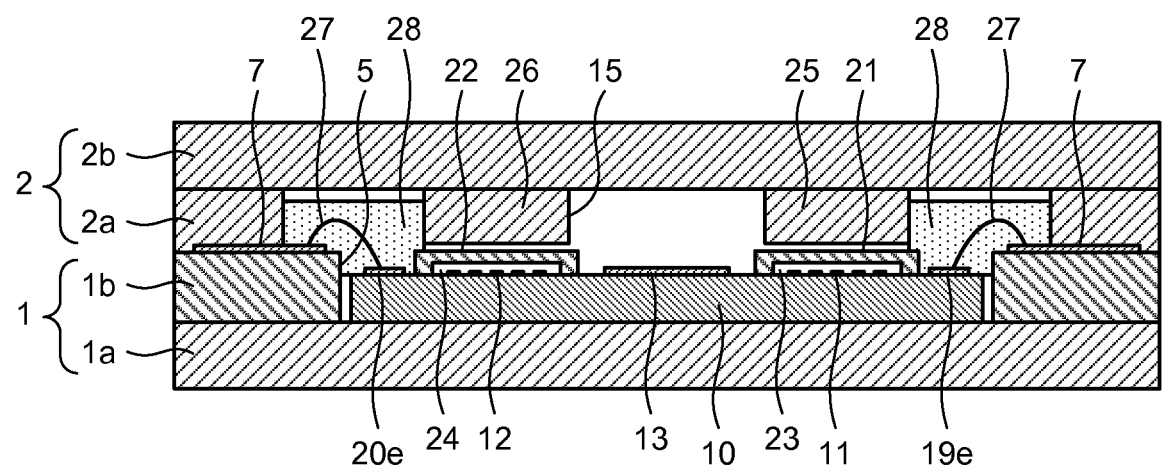
FIG. 4A is a cross-sectional view taken along line IVa-IVa' of FIG. 1.

The second IDT electrodes 12 are similarly covered with the second join member 22. Similarly to the first join member 21, the second join member 22 also is placed on the upper surface of the base 10 and has a hollow therein as illustrated in FIG. 4A. The hollow of the second join member 22 placed on the upper surface of the base 10 is a second oscillation space 24. The second IDT electrode 12 is sealed in the second oscillation space 24. This can separate the second IDT electrode 12 from the ambient air and the specimen and thus can protect the second IDT electrode 12. Securing the second oscillation space 24 can prevent the deterioration of the characteristic of the SAW received in the second IDT electrode 12.

Note that the shape of the oscillation space may be a rectangular parallelepiped, may be a dome as viewed in cross-sectional view, and may be an ellipse as viewed in planar view. The oscillation space may have an arbitrary shape in accordance with the shapes or arrangement of the IDT electrodes.

The first join member 21 includes a circular frame that surrounds the two first IDT electrodes 11 placed in the x direction and that is fixed on the upper surface of the base 10, and a lid that is fixed on the frame so as to cover the opening of the frame. Such a structure can be formed, for example, by patterning a resin film made of a photosensitive resin material, for example, with a photolithographic approach. The second join member 22 can be formed in a similar manner.

Note that, although the two first IDT electrodes 11 are covered with one first join member 21 in the sensor 100, the two first IDT electrodes 11 may be covered with two separate first join members 21. Alternatively, a partition may be provided between the two first IDT electrodes 11 while the two first IDT electrodes 11 are covered with one first join member 21. The two second IDT electrodes 12 may similarly be covered with separate second join members 22, or a partition may be provided between the two second IDT electrodes 12 while one second join member 22 is used.

To detect a specimen in the detection element 3 with the SAW, a predetermined voltage is applied to the first IDT electrodes 11 through the wires 7, the first connecting electrodes 19, and the like from the external measurement instrument. This excites the surface of the base 10 in the region in which the first IDT electrodes 11 are formed. This generates the SAW with a predetermined frequency. A part of the generated SAW propagates toward the detection unit 13, passes through the detection unit 13, and then reaches the second IDT electrode 12. When the specimen includes the first substance, the reaction caused by the first substance changes the second substance 200 included in the detection unit 13 and then the change varies the weight of the detection unit 13 as described in detail below. This alters the characteristic, such as the phase, of the SAW passing under the detection unit 13. When the SAW of which characteristic has been altered as described above reaches the second IDT electrode 12, a voltage in accordance with the SAW is generated in the second IDT electrode 12. The generated voltage is output to the outside through the second connecting electrode 20, the wire 7, and the like. Reading the output voltage with an external measurement instrument can examine a characteristics or ingredient of the specimen.

A capillary phenomenon is used in the sensor 100 in order to introduce the specimen to the detection unit 13. Specifically, joining the second cover member 2 to the first cover member 1 forms a long and narrow pipe at the groove 15 formed on the lower surface of the second cover member 2. For example, setting the width or diameter of the groove 15 at a predetermined value, for example, in consideration of the type of the specimen, or the material of the first cover member 1 and second cover member 2 can cause a capillary phenomenon in the long and narrow pipe formed of the groove 15. The groove 15 has a width (a dimension in the y direction), for example, of 0.5 mm to 3 mm, and a depth (a dimension in the z direction), for example, of 0.1 mm to 0.5 mm. Note that the groove 15 includes an extension portion 15e extending beyond the detection unit 13. The third through-hole 18 connected to the extension portion 15e is formed in the second cover member 2. The specimen flowing into the flow channel causes the air in the flow channel to be discharged to the outside from the third through-hole 18.

Such a pipe in which a capillary phenomenon arises is formed on the cover member including the first cover member 1 and the second cover member 2. Thus, merely making the specimen in contact with the inlet 14 causes the specimen to be sucked into the cover member through the groove 15 working as a flow channel. Thus, the sensor 100 can suck the specimen without a tool such as a pipette because the sensor 100 itself includes a mechanism of sucking the specimen therein. The part at which the inlet 14 is placed is rounded and the inlet 14 is formed on the top. This facilitates notice of the inlet 14.

Figure 4B:
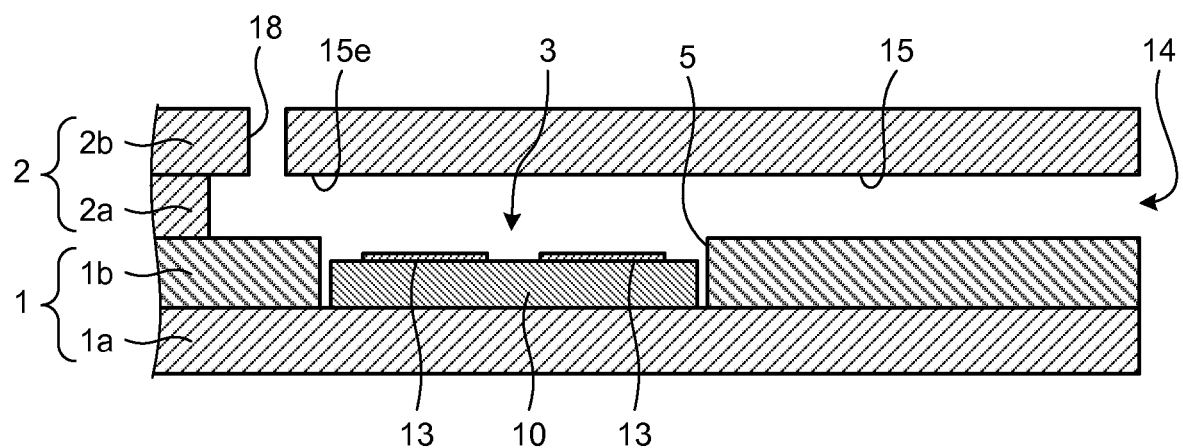
FIG. 4B is a cross-sectional view taken along line IVb-IVb' of FIG. 1.

By the way, the flow channel formed of the groove 15 has a depth of about 0.3 mm while the detection element 3 has a thickness of about 0.3 mm. The depth of the flow channel is almost the same as the thickness of the detection element 3. Thus, putting the detection element 3 on the flow channel without change blocks the flow channel. In light of the foregoing, the concave portion 5 on which the detection element 3 is installed is provided on the first cover member 1 in the sensor 100 as illustrated in FIGS. 4A and 4B. Accommodating the detection element 3 in the concave portion 5 can prevent the flow channel for the specimen from being blocked. In other words, setting the concave portion 5 so as to have a depth nearly equal to the thickness of the detection element 3 and then installing the detection element 3 in the concave portion 5 can secure the flow channel formed of the groove 15.

Figure 3:
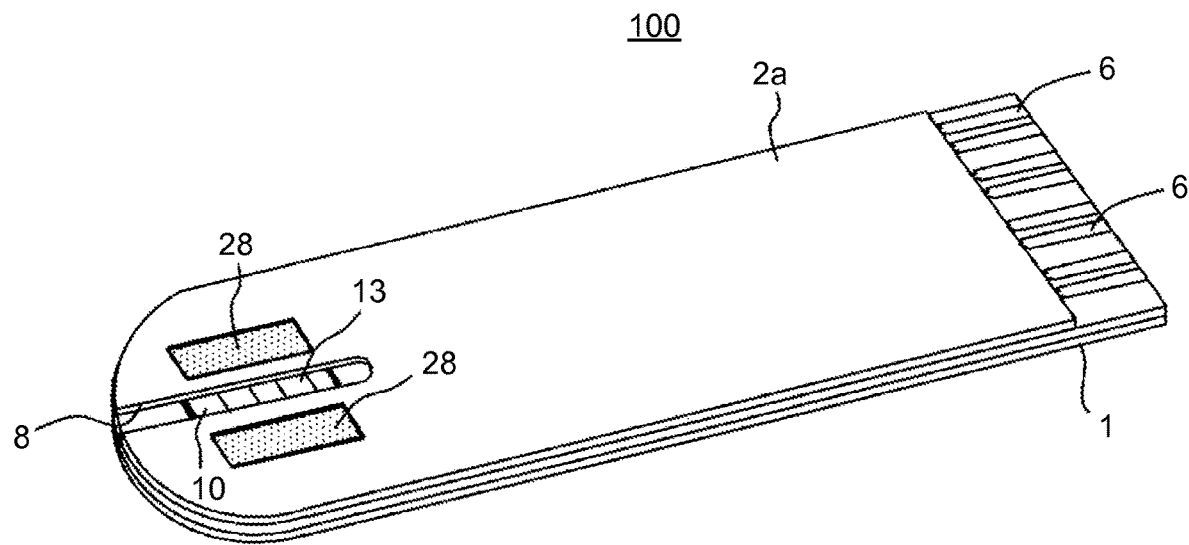
FIG. 3 is a perspective view of the sensor illustrated in FIG. 1 from which the fourth base is removed.

FIG. 3 is a perspective view of the sensor 100 from which the fourth base 2b of the second cover member 2 is removed. As illustrated in FIG. 3, the flow channel for the specimen is secured and the specimen that has flown into the flow channel can be smoothly guided to the detection unit 13 because of the capillary phenomenon.

In consideration of securing the flow channel for the specimen sufficiently, the height of the upper surface of the base 10 from the bottom surface of the concave portion 5 is preferably equal to or lower than the depth of the concave portion 5, as illustrated in FIGS. 4A and 4B. For example, the height of the upper surface of the base 10 from the bottom surface of the concave portion 5 is made equal to the depth of the concave portion 5. Then, the bottom surface of the flow channel can be placed at almost the same height as the detection unit 13 when the inside of the groove 15 is viewed from the inlet 14. The thickness of the base 10 is smaller than the depth of the concave portion 5 in the sensor 100 such that the heights of the first join member 21 and second join member 22 from the bottom surface of the concave portion 5 are nearly equal to the depth of the concave portion 5. When the heights of the first join member 21 and the second join member 22 from the bottom surface of the concave portion 5 are larger than the depth of the concave portion 5, it is necessary to process the first partition 25 and the second partition 26 of the third base 2a such that the partitions are thinner than the other parts. Such a process is not required when the heights of the first join member 21 and the second join member 22 from the bottom surface of the concave portion 5 are nearly equal to the depth of the concave portion 5. This can improve the production efficiency.

The flat surface of the concave portion 5 has a shape, for example, similar to the flat surface of the base 10. The concave portion 5 is slightly larger than the base 10 in size. More specifically, the concave portion 5 has such a size that a gap of about 100 μm can be formed between the side surface of the base 10 and the internal wall of the concave portion 5 when the base 10 is installed on the concave portion 5.

The detection element 3 is fixed on the bottom surface of the concave portion 5, for example, with a die bonding material mainly including epoxy resin, polyimide resin, or silicon resin. The end portion 19e of the first connecting electrode 19 is electrically connected to the wire 7 through a metal thin line 27 made, for example, of Au. The end portion 20e of the second connecting electrode 20 is connected to the wire 7 in a similar manner. Note that the first connecting electrode 19 and the second connecting electrode 20 can be connected to the wire 7 not only by the metal thin line 27, but also by, for example, a conductive adhesive material such as Ag paste.

A void is provided at each of the connections of the first connecting electrode 19 and the second connecting electrode 20, and the wires 7. This prevents the breakage of the metal thin line 27 when the second cover member 2 is stuck on the first cover member 1. The void can easily be formed by providing the first through-hole 16 and the second through-hole 17 in the third base 2a. The first partition 25 placed between the first through-hole 16 and the groove 15 can prevent the specimen flowing in the groove 15 from flowing into the void formed of the first through-hole 16. This can prevent the specimen from generating a short circuit among the first connecting electrodes 19. Similarly, the second partition 26 placed between the second through-hole 17 and the groove 15 can prevent the specimen flowing in the groove 15 from flowing into the void formed of the second through-hole 17. This can prevent the specimen from generating a short circuit among the second connecting electrodes 20.

The first partition 25 is placed on the first join member 21. The second partition 26 is placed on the second join member 22. Thus, more strictly speaking, the flow channel for the specimen is defined not only with the groove 15 but also with the sidewall of the first join member 21 on the groove side and the sidewall of the second join member 22 on the groove side. In consideration of preventing the leakage of the specimen to the voids formed of the first through-hole 16 and the second through-hole 17, the first partition 25 is preferably in contact with the upper surface of the first join member 21 and the second partition 26 is preferably in contact with the upper surface of the second join member 22. However, the sensor 100 includes gaps between the lower surface of the first partition 25 and the upper surface of the first join member 21, and between the lower surface of the second partition 26 and the upper surface of the second join member 22. Each of the gaps is, for example, 10 μm to 60 μm. For example, if the sensor 100 is pinched with fingers and a pressure is added (applied) to the pinched part, the provided gaps can prevent the pressure from directly being added (applied) to the first join member 21 and the second join member 22 by absorbing the pressure. This can prevent the first oscillation space 23 and the second oscillation space 24 from largely deforming. The specimen normally has a certain level of viscoelasticity. Thus, keeping the gap at 10 μm to 60 μm prevents the specimen from flowing into the gap easily. This can prevent the leakage of the specimen to the voids formed of the first through-hole 16 and the second through-hole 17.

The first partition 25 has a width larger than the first oscillation space 23. In other words, the sidewall of the first partition 25 is placed on the frame of the first join member 21. Thus, the frame supports the first partition 25 if an external pressure makes the first partition 25 in contact with the first join member 21. This can prevent the first join member 21 from deforming. For the same reason, the second partition 26 preferably has a width larger than the first oscillation space 23.

The first connecting electrodes 19, the second connecting electrodes 20, the metal thin lines 27, and the wires 7, which are placed in the voids formed of the first through-hole 16 and the second through-hole 17, are covered with an insulating members 28. Covering the first connecting electrodes 19, the second connecting electrodes 20, the metal thin lines 27, and the wires 7 with the insulating members 28 can prevent the corrosion of the components such as the electrodes. Providing the insulating members 28 blocks the specimen if the specimen flows into the space between the first partition 25 and the first join member 21, or the space between the second partition 26 and the second join member 22. This can prevent, for example, the leakage of the specimen from causing a short circuit among the connecting electrodes.

As described above, the sensor 100 can secure the flow channel for the specimen from the inlet 14 to the detection unit 13 by accommodating the detection element 3 in the concave portion 5 of the first cover member 1. Thus, the specimen, which has been sucked from the inlet, can be sent to the detection unit 13, for example, by a capillary phenomenon. In other words, a sensor 100 including a suction mechanism can be provided while using a thick detection element 3.

Figure 7:
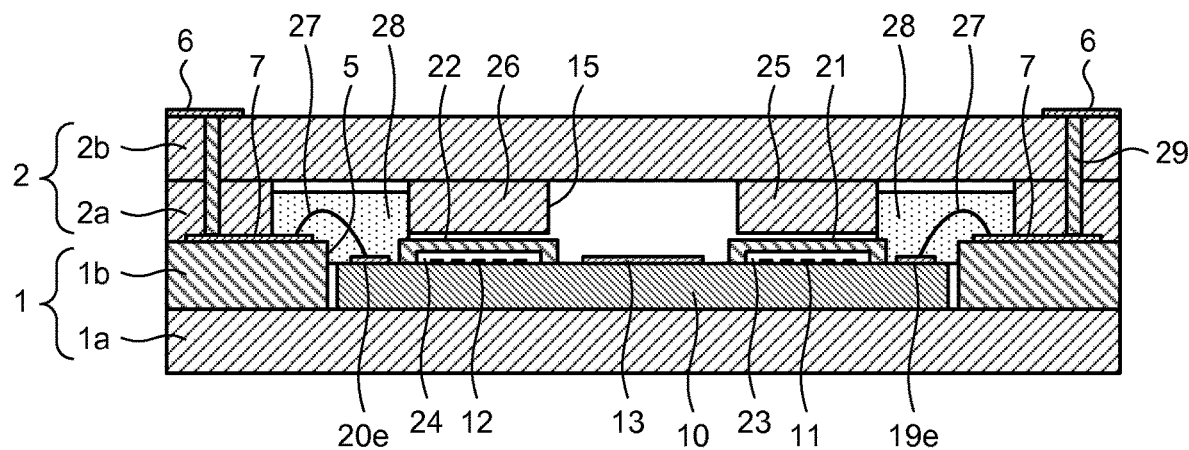
FIG. 7 is a cross-sectional view of an exemplary variation of the sensor according to the embodiment of the present invention.

FIG. 7 is a cross-sectional view of an exemplary variation of the sensor 100. The cross-sectional view corresponds to the cross-sectional view of FIG. 4A.

The placement of the terminals 6 is changed in the exemplary variation. The terminals 6 are formed on the upper surface of a fourth base 2*b* in the exemplary variation whereas the terminals 6 are formed at the longitudinal second end portion of the second base 1*b* in the embodiment described above. Each of the terminals 6 and each of the wires 7 are electrically connected through a through conductor 29 penetrating a second cover member 2. The through conductor 29 is made, for example, of Ag paste, or plating. Alternatively, the terminals 6 can be formed on the lower surface side of the first cover member 1. Thus, each of the terminals 6 can be formed at an arbitrary position on the surfaces of the first cover member 1 and the second cover member 2. The position can be determined in accordance with the used measurement instrument.

Figure 8:
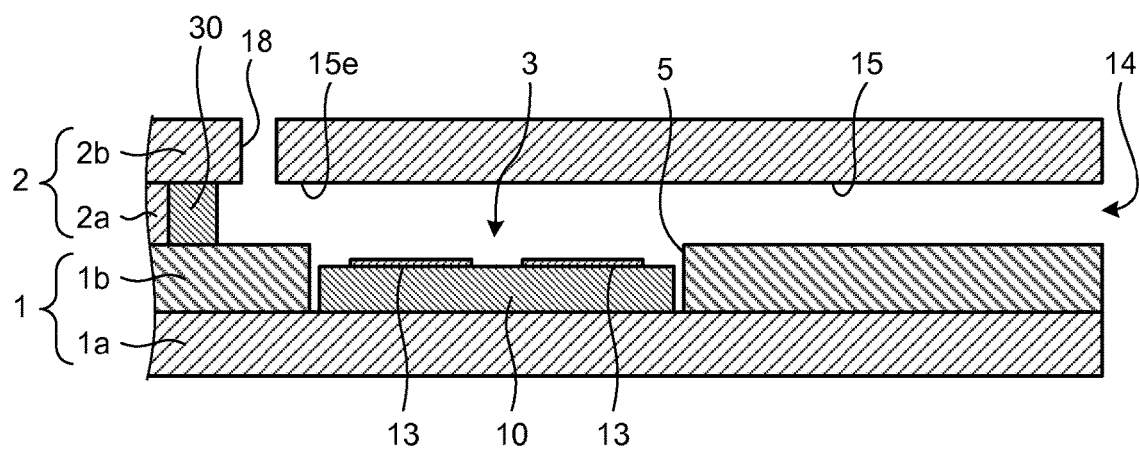
FIG. 8 is a cross-sectional view of another exemplary variation of the sensor according to the embodiment of the present invention.

FIG. 8 is a cross-sectional view of another exemplary variation of the sensor 100. The cross-sectional view corresponds to the cross-sectional view of FIG. 4B.

The exemplary variation is provided with an absorber 30 at an end of a flow channel formed of the groove 15. The absorber 30 absorbs the specimen at a predetermined speed. Providing the absorber 30 can implement a stable measurement by absorbing an excess amount of the specimen and maintaining a constant amount of the specimen flowing on the detection unit 13. The absorber 30 is made, for example, of a porous material, such as a sponge, that can absorb liquid.

Note that the configurations of the sensor 100 described above are examples. The configuration of the sensor 100 is not limited to the examples. An arbitrary sensor 100 can be used. If a metal film is not required in order to immobilize the second substance 200 on the detection unit 13 provided on the upper surface of the base, a metal film does not have to be used. In other words, the detection unit 13 can be formed by immobilizing the second substance 200 at the region between a first IDT electrode 11 and a second IDT electrode 12 on the surface of the base 10 without a metal film. The base 10 is a piezoelectric base.

The detection element 3 including a surface acoustic wave device has been described as an example in the embodiment. The detection element 3 is not limited to the example. For example, the detection element 3 in which an optical waveguide used to cause surface plasmon resonance is formed can be used. In that case, for example, the variations in refractive index of the light in the detection unit are read. Additionally, a detection element 3 in which an oscillator is formed on a piezoelectric base made of crystal can also be used. In that case, for example, the variations in oscillation frequency of the oscillator are read.

Alternatively, for example, a plurality of types of devices can be placed on a base as a detection element 3. For example, an enzyme electrode with an enzyme electrode method can be provided next to the SAW device. This enables a measurement with an enzyme method in addition to an immunization method with an antibody or an aptamer and thus can increase the number of items to be tested at a time.

An example in which the first base 1*a* and the second base 1*b* form the first cover member 1, and the third base 2*a* and the fourth base 2*b* form the second cover member 2 has been described in the embodiment. However, the bases are not limited to the example. Some of the bases may be integrated. For example, a first cover member 1 formed of integrated first base 1*a* and second base 1*b* can be used.

An example in which a detection element 3 is provided has been described in the embodiment. However, a plurality of detection elements 3 can be provided. In that case, each detection element 3 may be provided with a concave portion 5. Alternatively, a long concave portion 5 that can accommodate all of the detection elements 3 may be formed.

Furthermore, the groove 15 can be provided either on the first cover member 1 or on the second cover member 2, or can be provided on both of the first cover member 1 and the second cover member 2. For example, providing grooves on both of the first cover member 1 and the second cover member 2 may form the flow channel. Alternatively, providing a groove on one of the first cover member 1 and the second cover member 2 may form the flow channel.

An example in which the base 10 is provided on the first cover member 1 and the first cover member 1 is joined to the second cover member 2 has been described in the embodiment. However, the base is not limited to the example. For example, joining a cover portion directly to the base 10 may form the flow channel.

With reference to FIG. 9 to FIGS. 11A and 11B, the base 10 to which a cover member 45 is directly joined will be described. An example in which providing a groove on the cover member 45 joined to a base 10A forms the flow channel will be described with reference to FIG. 9 to FIGS. 11A and 11B. However, the formation is not limited to the example. For example, providing grooves on both of the cover member 45, which is provided on the upper surface of the base 10A, and the base 10A may form the flow channel. Alternatively, providing a groove on the base 10A may form the flow channel.

Figure 9:
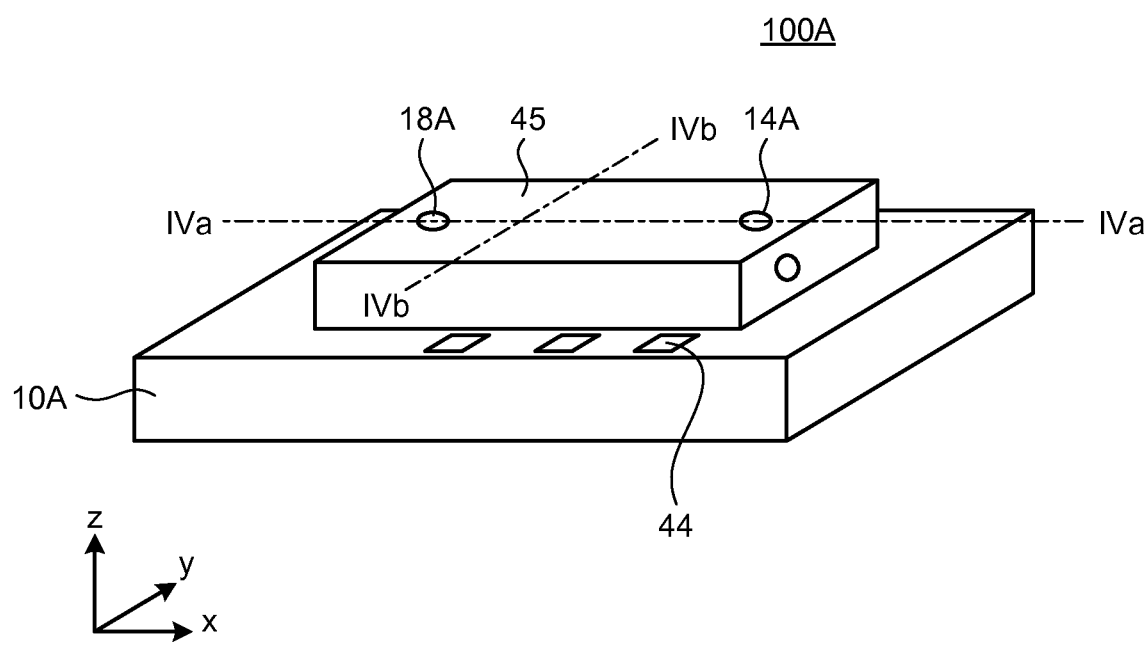
FIG. 9 is a perspective view of an exemplary sensor in which the cover member is joined to the base.

FIG. 9 is a perspective view of an exemplary sensor in which the cover member is joined to the base. In the example illustrated in FIG. 9, a sensor 100A includes the base 10A and the cover member 45. The cover member 45 includes an inlet 14A for the specimen, and a third through-hole 18A working as an air duct or an outlet for the specimen. Note that, although the inlet 14A is provided on the upper surface of the cover member 45 in the example illustrated in FIG. 9, the inlet 14A is not limited to the example. For example, the inlet 14A may be provided on the side surface of the cover member 45, similarly to the case of the sensor 100. Note that the base 10A includes pads 44 in the example illustrated in FIG. 9. The pads 44 correspond, for example, to the end portions 19e of the first connecting electrodes 19 or the end portions 20e of the second connecting electrodes 20 in the sensor 100.

Figure 10:
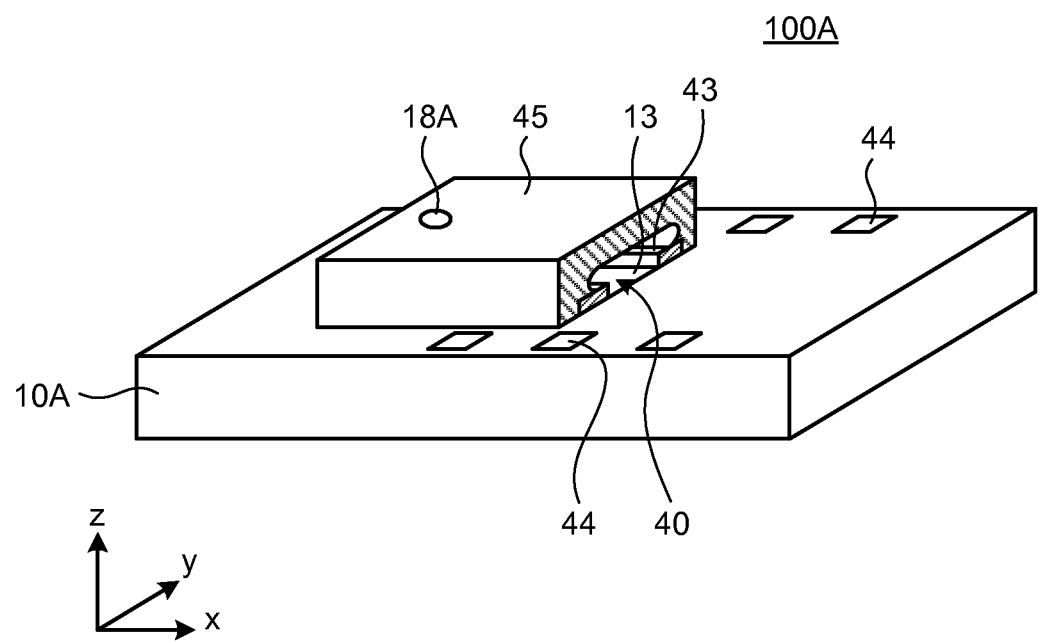
FIG. 10 is a perspective view of an exemplary sensor from which a half of the cover member is removed.

FIG. 10 is a perspective view of an exemplary sensor from which a half of the cover member is removed. As illustrated in FIG. 10, the perspective view illustrates the sensor 100A from which a half of the cover member 45 is removed. As illustrated in FIG. 10, a space 40 is formed in the cover member 45. The space 40 works as a flow channel for the specimen. The inlet 14A is connected to the space 40. In other words, the specimen flows from the inlet 14A into the space 40. Note that the space 40 in the sensor 100A corresponds to the flow channel in the sensor 100.

Figure 11A:
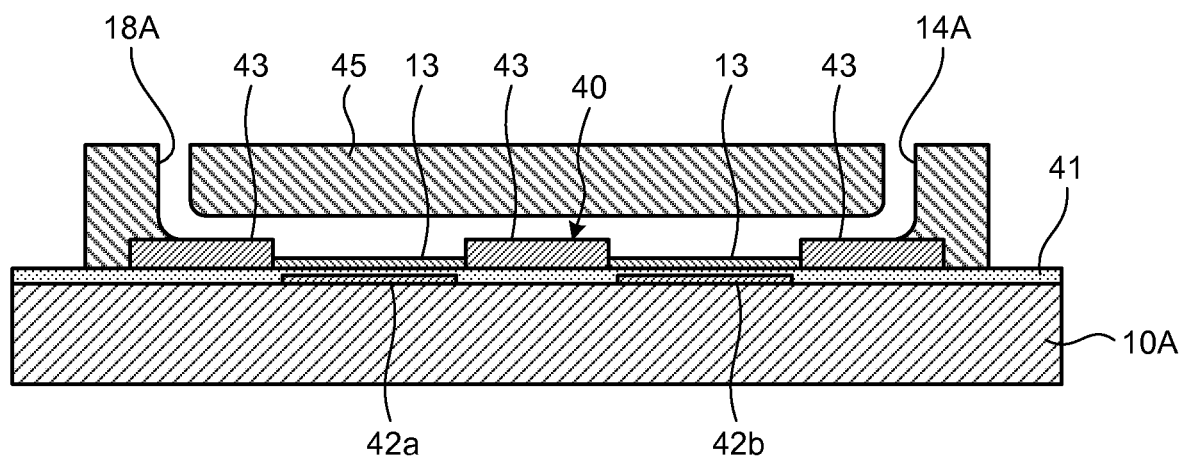
FIG. 11A is a cross-sectional view of an exemplary sensor in which the cover member is joined to the base.
Figure 11B:
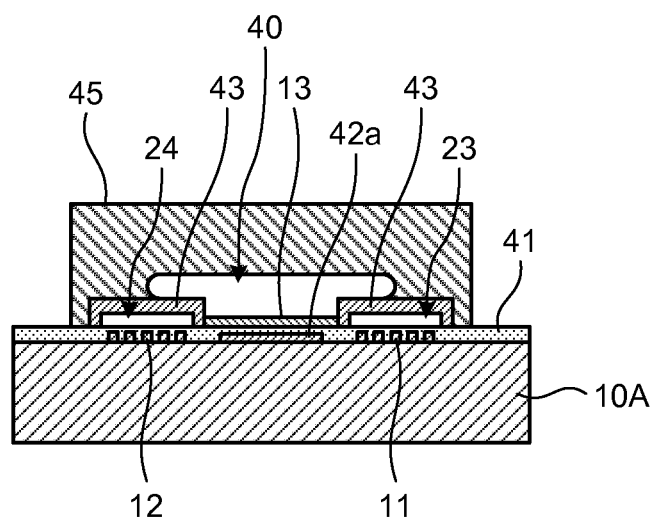
FIG. 11B is a cross-sectional view of an exemplary sensor in which the cover member is joined to the base.

FIGS. 11A and 11B are cross-sectional views of an exemplary sensor in which the cover member is joined to the base. FIG. 11A is a cross-sectional view taken along line IVa-IVa of FIG. 9. FIG. 11B is a cross-sectional view taken along line IVb-IVb of FIG. 9.

As illustrated in FIGS. 11A and 11B, for example, the first IDT electrode 11, the second IDT electrode 12, a short-circuit electrode 42a, and a short-circuit electrode 42b are provided on the upper surface of the base 10A. The first IDT electrode 11, the second IDT electrode 12, the short-circuit electrode 42a, and the short-circuit electrode 42b are covered with a protection film 41. The protection film 41 contributes, for example, to the prevention of oxidation of each electrode and wire. The protection film 41 is made, for example, of silicon oxide, aluminum oxide, zinc oxide, titanium oxide, silicon nitride, or silicon. The protection film 41 is made, for example, of silicon dioxide ($SiO_2$).

The protection film 41 is formed on the whole upper surface of the base 10A while exposing the pads 44. Covering the first IDT electrode 11 and the second IDT electrode 12 with the protection film 41 can prevent the corrosion of the IDT electrodes.

The protection film 41 has a thickness, for example, of 100 nm to 10 μm. Note that the protection film 41 is not necessarily formed on the whole upper surface of the base 10A. For example, the protection film 41 may be formed so as to cover only the vicinity of the center of the upper surface of the base 10A such that the region including the pads 44 and extending along the outer periphery of the upper surface of the base 10A is exposed. The protection film 41 is used in the example illustrated in FIGS. 11A and 11B. However, the sensor is not limited to the example. The protection film 41 does not have to be used.

The short-circuit electrode 42a and the short-circuit electrode 42b are used to develop an electrical short circuit at the part working as a propagation channel of SAW on the upper surface of the base 10A. Providing the short-circuit electrode 42a or the short-circuit electrode 42b can reduce the loss of some types of SAW. Note that the short-circuit electrode 42a or the short-circuit electrode 42b more efficiently prevents the loss of a Leaky wave used as the SAW especially.

The short-circuit electrode 42a and the short-circuit electrode 42b each have, for example, a rectangular shape extending along the propagation channel of the SAW from the first IDT electrode 11 toward the second IDT electrode 12. The short-circuit electrode 42a and the short-circuit electrode 42b each have a width in the direction orthogonal to the direction in which the SAW propagates (the x direction), for example, equal to the intersectional width between the electrode fingers of the first IDT electrode 11. The end portions of the short-circuit electrode 42a and the short-circuit electrode 42b on the first IDT electrode side are each placed at a position a half wave length of SAW away from the center of the electrode finger placed at the end portion of the first IDT electrode 11 in the direction parallel to the direction in which the SAW propagates (the y direction). Similarly, the end portions of the short-circuit electrode 42a and short-circuit electrode 42b on the second IDT electrode side in the y direction are each placed at a place a half wave length of SAW away from the center of the electrode finger placed at the end portion of the second IDT electrode 12.

The short-circuit electrode 42a and the short-circuit electrode 42b may electrically flow or may be provided with the pad 44 for ground potential and connected to the pad 44 so as to be at ground potential. The short-circuit electrode 42a and short-circuit electrode 42b at ground potential can prevent the propagation of the direct wave caused by the electromagnetic coupling between the first IDT electrode 11 and the second IDT electrode 12.

The short-circuit electrode 42a and the short-circuit electrode 42b are made, for example, of aluminum or an alloy of aluminum and copper. The electrodes may have a multi-layer structure. The multi-layer structure has, for example, a first layer made of titanium or chrome, and a second layer made of aluminum or an aluminum alloy.

The board bodies 43 include concave portions in which the first oscillation space 23 and the second oscillation space 24 are formed. Joining the board bodies 43 to the base 10A forms the first oscillation space 23 and the second oscillation space 24. The board body 43 is made, for example, of a photosensitive resist. The board bodies 43 correspond to the first join member 21 and the second join member 22 in the sensor 100. In the example illustrated in FIGS. 11A and 11B, penetrating portions penetrating the board bodies 43 in the thickness direction is formed between the concave portions forming the first oscillation space 23 and the second oscillation space 24 in the board bodies 43. The penetrating portions are provided for forming the detection units 13 on the propagation channel of the SAW. In other words, when the board bodies 43 are joined to the base 10A, at least a part of the propagation channel of the SAW propagating from the first IDT electrode 11 to the second IDT electrode 12 is exposed from the penetrating portions as viewed in planar view. The detection units 13 are provided at the exposed part.

Figure 12:
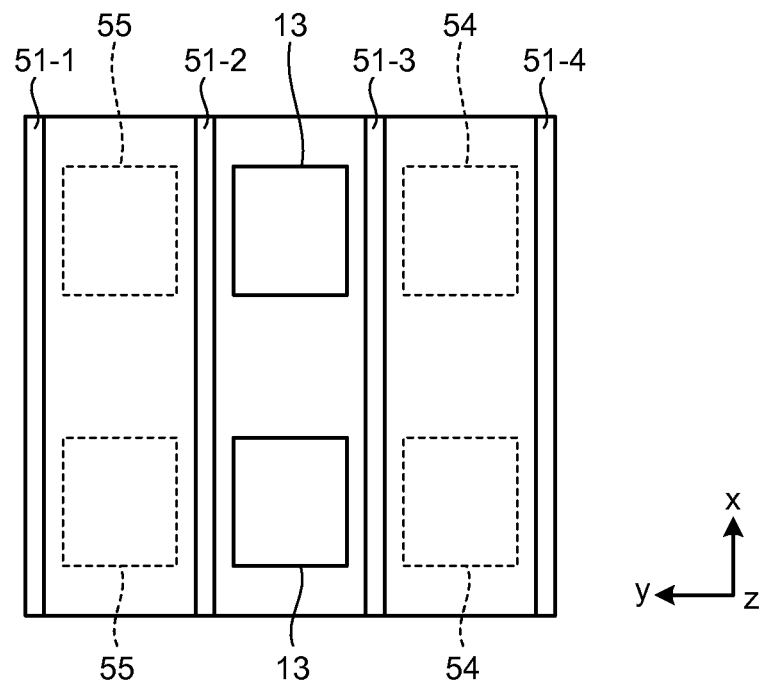
FIG. 12 is a plan view of another example in which the cover member is joined to the base.
Figure 13:
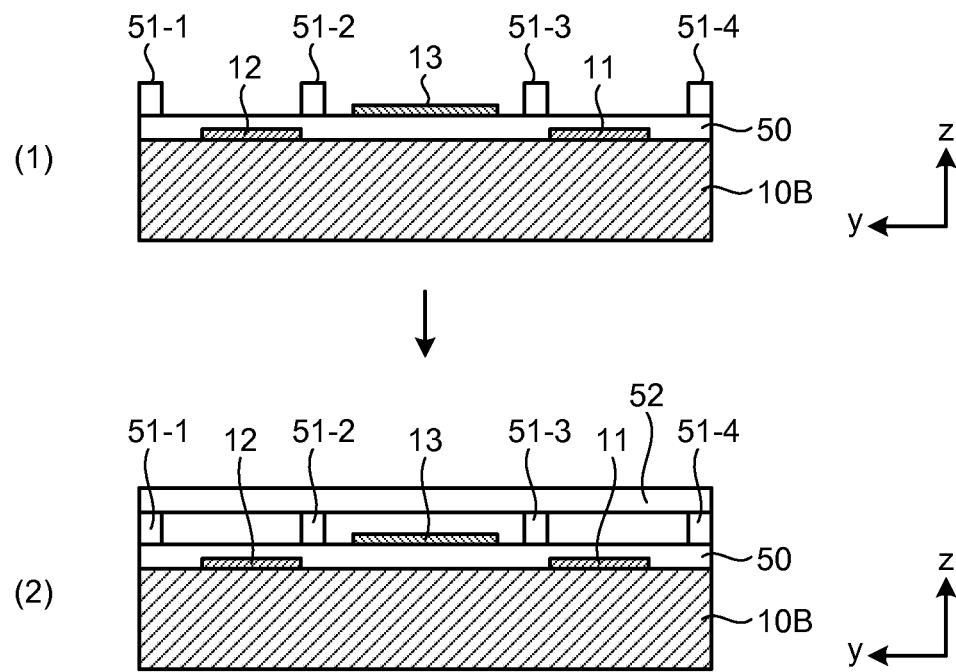
FIG. 13 is a cross-sectional view of another example in which the cover member is joined to the base.

With reference to FIGS. 12 and 13, another example in which the cover member is joined to the base will be described. FIG. 12 is a plan view describing another example in which the cover member is joined to the base. FIG. 12 is a plan view illustrating an x-y plane.

As illustrated in FIG. 12, a base 10B includes two detection units 13, and convex portions 51-1 to 51-4 extending in the x-axis direction. In the example illustrated in FIG. 13, a first IDT electrode 11 and a second IDT electrode 12 are provided at lower parts of a portion 54 and portion 55 in the base surface of the base 10B. The example illustrated in FIG. 12 includes four convex portions 51. Arranging convex portions 51 in parallel separates the part provided with a detection unit 13 from the part provided with the portion 54 or the portion 55 in the base surface. However, the arrangement is not limited to the example. The convex portions 51 may not be arranged in parallel. The example illustrated in FIG. 12 does not have to include the convex portion 51-1 and the convex portion 51-4.

In that case, the convex portions 51-1 to 51-4 are formed, for example, with photolithography. As a more detailed example, the base surface of the base 10B is covered with an arbitrary resist, and then unnecessary parts of the resist are removed such that the convex portions 51-1 to 51-4 are formed. This forms the convex portions 51-1 to 51-4. Each of the convex portions 51-1 to 51-4 may have an arbitrary length in the z-axis direction. The length is preferably 30 to 100 μm.

FIG. 13 is a cross-sectional view of another example in which the cover member is joined to the base. FIG. 13 is a cross-sectional view taken along a y-z plane. The example illustrated at a part (1) in FIG. 13, the base 10B includes a first IDT electrode 11 and a second IDT electrode 12 on its base surface. The base surface of the base 10B is covered with a protection film 50 that contributes, for example, to the prevention of oxidation of each electrode and wire. The protection film 50 corresponds to the protection film 41. The base 10B further includes the detection unit 13 and convex portions 51-1 to 51-4 on the protection film 50 covering the base surface. At that time, the second substance 200 is immobilized on the detection unit 13 of the base 10B.

Then, as illustrated at a part (2) in FIG. 13, a cover member 52 is joined to the base 10B in which the second substance 200 is immobilized on the detection unit 13. This forms a flow channel and oscillation spaces. Specifically, the convex portions 51-1 to 51-4 provided on the base 10B are joined to the cover member 52. This forms a groove used to guide the specimen to the detection unit 13 and forms the oscillation spaces on the IDT electrodes.

The convex portions 51-1 to 51-4 may be joined to the cover member 52 in an arbitrary method. For example, an ultraviolet adhesive may be used for the joining. The cover member 52 may be made of an arbitrary material. The material is preferably a hydrophilic material, and more preferably a hydrophilic film. Alternatively, a material of which surface is hydrophilically-treated can be used. Specifically, the surface of the material can be hydrophilically-treated by a plasma treatment or a process with a silane coupling agent.

The surface exposed to the inside of the flow channel is configured to have a hydrophilic degree so as to keep the contact angle of 50 degrees or lower with water. This facilitates smooth suction of the specimen by a capillary phenomenon. The angle is preferably 30 degrees or lower. It has been confirmed that the surface treatment is performed such that the internal wall of the flow channel have a contact angle of 30 degrees or lower provides a good suction mechanism.

Note that, for example, the detection unit 13 may be treated with an arbitrary process. For example, the detection unit 13 may be treated with a process for preventing a material from adhering. For example, on the assumption that nucleic acid such as DNA is negatively charged, the metal film of the detection unit 13 is negatively charged with an arbitrary method. This can prevent nucleic acid such as DNA from adhering. Similarly, on the assumption that nucleic acid such as DNA tends to adhere to gold, a metal film made of a metal other than gold can be used as the metal film of the detection unit 13 if the detection unit 13 is used as a reference.

The sensor described above is effective, for example, for detecting a hydrogen peroxide source. As a detailed example, the sensor can be used for general purposes such as beauty or the maintenance of youth as a fatigue marker, and an anti-aging marker in addition to conventional medical purposes as a cancer marker. An embedded SAW chip working as a high-sensitive transducer is used as a disposable sensor. This can implement a light, thin, and downsized sensor that can easily detect a hydrogen peroxide source and that is appropriately disposable.

For example, the propagation channel for the SAW that is a portion in which the SAW acts with a biological material, and an IDT electrode that is a unit converting the SAW into an electric signal can be finely produced on a base. This can significantly downsize the sensor. The sensor can be mass-produced, for example, with wafer processing. This can easily implement a disposable sensor chip.

For example, on the assumption that an SAW sensor propagates signals in a high frequency range, selecting the frequency or the length of the propagation channel can select a necessary sensitivity. This can also increase the types of tests or the test range.

For example, the circuit for detecting the SAW has the same circuit configuration as the circuit configurations used in the communication apparatuses in many wireless terminals or tablet terminals. Thus, the sensor described above can easily be connected to an electric appliance such as a wireless terminal or a tablet terminal.

[Embodiment of Detection Unit of Sensor]

The disclosed sensor 100 includes a detection unit 13 on which a second substance 200 is immobilized in an embodiment. The second substance 200 includes a bond that is cleft by the reaction with hydrogen peroxide. In an embodiment of the sensor 100, the specimen in contact with an enzyme that generates hydrogen peroxide by the reaction with the first substance is introduced into the detection unit 13.

In that case, the first substance is an arbitrary material that is a substrate of an enzyme that generates hydrogen peroxide. The first substance is preferably a material without antigenicity such as protein or glucose. The first substance is, for example, sugar, lipid, metabolite, or a low-molecular-weight organic compound.

The enzyme used in the disclosed sensor 100 generates hydrogen peroxide by the reaction with the first substance. Specifically, in the enzymes used in the disclosed sensor 100, a dissolved enzyme dissolved in the specimen generates hydrogen peroxide with the first substance working as a substrate by oxidation reaction. An enzyme used in the disclosed sensor 100 is, for example, oxidase. As more detailed example, the enzyme is galactose oxidase, glucose oxidase, cholesterol oxidase, amine oxidase, various types of amino-acid oxidase, polyphenol oxidase, xanthine oxidase, or uricase. Note that peroxidase is an enzyme consuming hydrogen peroxide, and thus does not correspond to the enzyme used in the disclosed sensor 100.

An exemplary correspondence relationship between the first substance and the enzyme will be described hereinafter. For example, when the first substance is glucose, glucose oxidase is used as the enzyme. For example, when the first substance is cholesterol, cholesterol oxidase is used as the enzyme.

The specimen is a solution to be detected whether the solution includes the first substance. The specimen can be an arbitrary solution including a liquid or solid to be detected. When the material to be detected is liquid, the specimen can be the liquid to be detected.

The specimen comes in contact with an enzyme by previously adding in and mixing the enzyme with the specimen. Alternatively, the specimen comes in contact with an enzyme adhering or immobilized to the flow channel of the sensor 100 by passing through the flow channel of the sensor 100. In other words, the specimen in contact with an enzyme is, for example, the specimen to which the enzyme is previously added, or the specimen that passes through the flow channel of the sensor 100 and then comes in contact with the enzyme adhering or immobilized to the flow channel of the sensor 100.

The second substance 200 includes a bonding portion 210 of which bond is cleft by the reaction with hydrogen peroxide. The second substance 200 includes boronic acid ester including a bond that is cleft by the reaction with hydrogen peroxide, and further includes boronic acid at a separation part that is separated from the detection unit 13 by the cleavage of the bond by the reaction with the hydrogen peroxide. The second substance 200 is preferably a compound expressed by the following general formula (1), or a boron compound expressed by the following general formula (2). Note that a phenylboronic acid ester compound expressed by the following general formula (3) is an exemplary boron compound that can stably exist in water in the general formula (2).

[Formula 1]

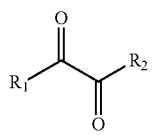
(1)

[Formula 2]

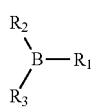
(2)

[Formula 3]

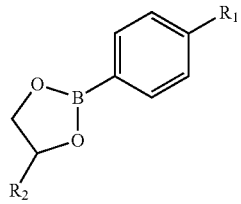
(3)

The $R_1$, $R_2$, and $R_3$ in the formulae (1) and (2) independently indicate an alkyl group, an aryl group, an alkoxy group or an aryloxy group. However, they can indicate others.

The bonding portion 210 of which bond is cleft by the reaction with hydrogen peroxide is, for example, a bond between two carbonyl groups in the case of the general formula (1), a bond between B and R1, R2, or R3 in the case of the general formula (2), or a bond between B and a phenyl group in the case of the general formula (3).

Alternatively, a compound expressed by the following general formula (4) or boronic acid ester expressed by the following general formula (5) is also preferably be used.

[Formula 4]

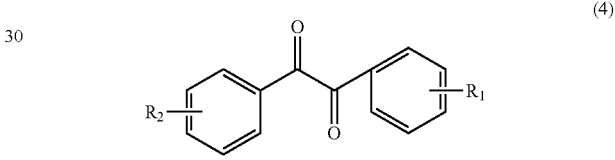
(4)

[Formula 5]

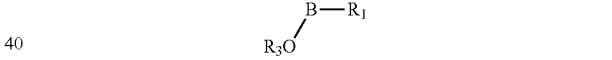
(5)

The R1, and R2 in the formula (4) independently indicate an alkyl group, or an aryl group. In the formula (5), the R1 indicates an aryl group, and the R2 and R3 independently indicate an alkyl group and an aryl group. The R2 and R3 may form a ring by binding to each other. One of the R2 and R3 may be an hydrogen atom. The compound expressed by the formula (4) is preferable because the phenyl groups symmetrically bind to each other while holding the carbonyl group therebetween.

The second substance 200 preferably includes nanoparticles at the separation part that is separated from the detection unit 13 by the cleavage of the bond by the reaction with hydrogen peroxide. In other words, the second substance 200 includes nanoparticles 221 at a separation part 220 that is separated from the detection unit 13 by the cleavage of the bond of the bonding portion 210. When the second substance 200 includes the nanoparticles 221 in the separation part 220 and the bond in the bonding portion of the second substance 200 is cleft, the nanoparticles 221 separate from the detection unit 13. This can increase the variations in state of the base surface in comparison with the case without the nanoparticles 221.

The nanoparticles 221 are preferably made, for example, of an arbitrary material such as gold, silver, iron, aluminum, tin, platinum, chrome, nickel, or latex or a plurality of the materials with an arbitrary method. The nanoparticles 221 preferably have a particle diameter of 100 nm or less.

The nanoparticles 221 are preferably a material to which protein or the like does not non-specifically absorb. For example, gold nanoparticles are used preferably after their surfaces are blocked, for example, with Secondary Butyl Alcohol (SBA), bovine serum albumin (BSA), lactoprotein, or Poly Ethylene Glycol (PEG). In other words, the gold nanoparticles of which surfaces are covered with SBA or PEG is preferably used. Note that latex nanoparticles are more preferable than unblocked gold nanoparticles because it is known that latex nanoparticles have a non-specific absorption smaller than that of the unblocked gold nanoparticles. However, it is also preferable to block the latex nanoparticles with a blocking process.

When the second substance 200 is a compound including boronic acid ester, it is preferable that the second substance 200 is immobilized on the detection unit 13 such that the separation part 220 includes the boronic acid. The separation part 220 is separated from the detection unit 13 when the bond is cleft by the reaction with hydrogen peroxide. For example, when the second substance 200 can be expressed by the general formula (1) or (2), the end portion of the R1 is preferably immobilized on the detection unit 13. In other words, sugar such as glucose and phenylboronic acid sometimes form a complex. In that case, any complex formed of sugar such as glucose and phenylboronic acid possibly prevents the hydrogen peroxide from cleaving the bonding portion of the second substance 200, or possibly varies the state of the base surface due to the glucose forming the complex. In light of the foregoing, a boron atom is included in the separation part 220 to be separated from the detection unit 13. Thus, if a complex is formed, the complex is formed with the separation part 220 to be separated from the detection unit 13. This can suppress an effect on the variations in state of the base surface. The variations are caused when the hydrogen peroxide described below cleaves the bonding portion of the second substance 200.

Figure 14:
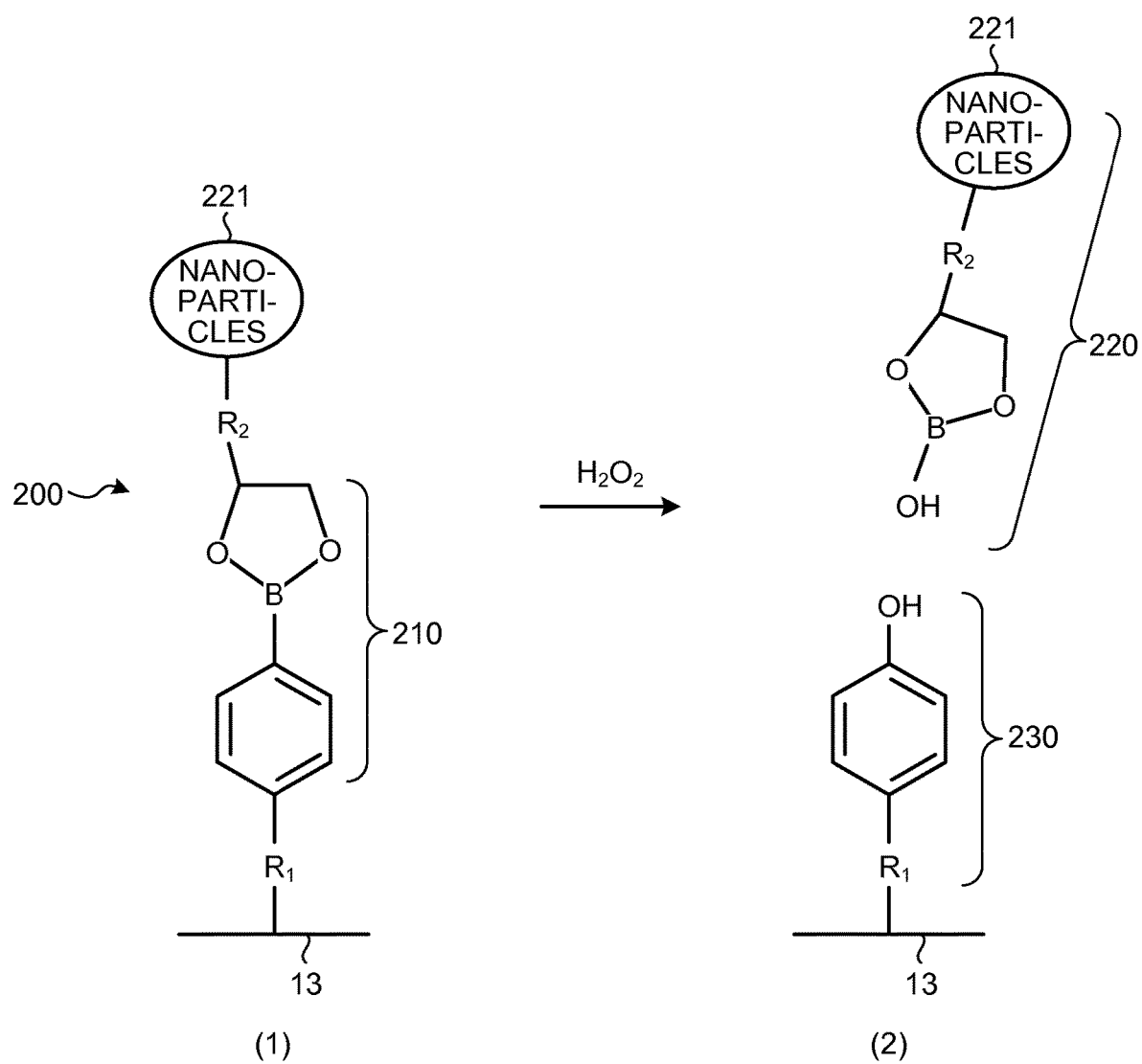
FIG. 14 is an explanatory view of an exemplary sensor according to the embodiment of the present invention.

FIG. 14 is an explanatory view of an exemplary sensor according to the embodiment of the present invention. For the sake of description, the second substance 200 includes a phenylboronic acid ester area working as the bonding portion 210 of which bond is cleft by the reaction with hydrogen peroxide, and nanoparticles 221 in the example at a part (1) in FIG. 14. The example in FIG. 14 is illustrated together with the surface of the detection unit 13 for the sake of description.

If no substrate of an enzyme that generates hydrogen peroxide exists in the specimen, the second substance 200 immobilized on the detection unit 13 remains without change as illustrated at the part (1) in FIG. 14. On the other hand, if the substrate of an enzyme that generates hydrogen peroxide exists in the specimen, the hydrogen peroxide cleaves the bonding portion 210 and thus the separation part 220 including the nanoparticles 221 separates from the detection unit 13 as illustrated a part (2) in FIG. 14. If the substrate of an enzyme that generates hydrogen peroxide exists in the specimen, a part 230, which is obtained by removing the separation part 220 onward from the bonding portion 210 from the second substance 200, remains and is immobilized on the surface of the detection unit 13 as illustrated the part (2) in FIG. 14. Consequently, the molecular weight of the second substance 200 immobilized on the base surface varies. This varies the state of the base surface.

In that case, the detection unit 13 may be the whole surface of the base surface, or may be a part of the base surface. The detection unit 13 includes, for example, a metal film, and a second substance 200 immobilized on a metal film. However, the detection unit 13 is not limited to the example. The detection unit 13 does not have to include a metal film. When the detection unit 13 includes a metal film, the metal film may be made of an arbitrary metal. The metal film, for example, may be made of Au, Ti, or Cu, and is preferably made of Au.

Figure 15:
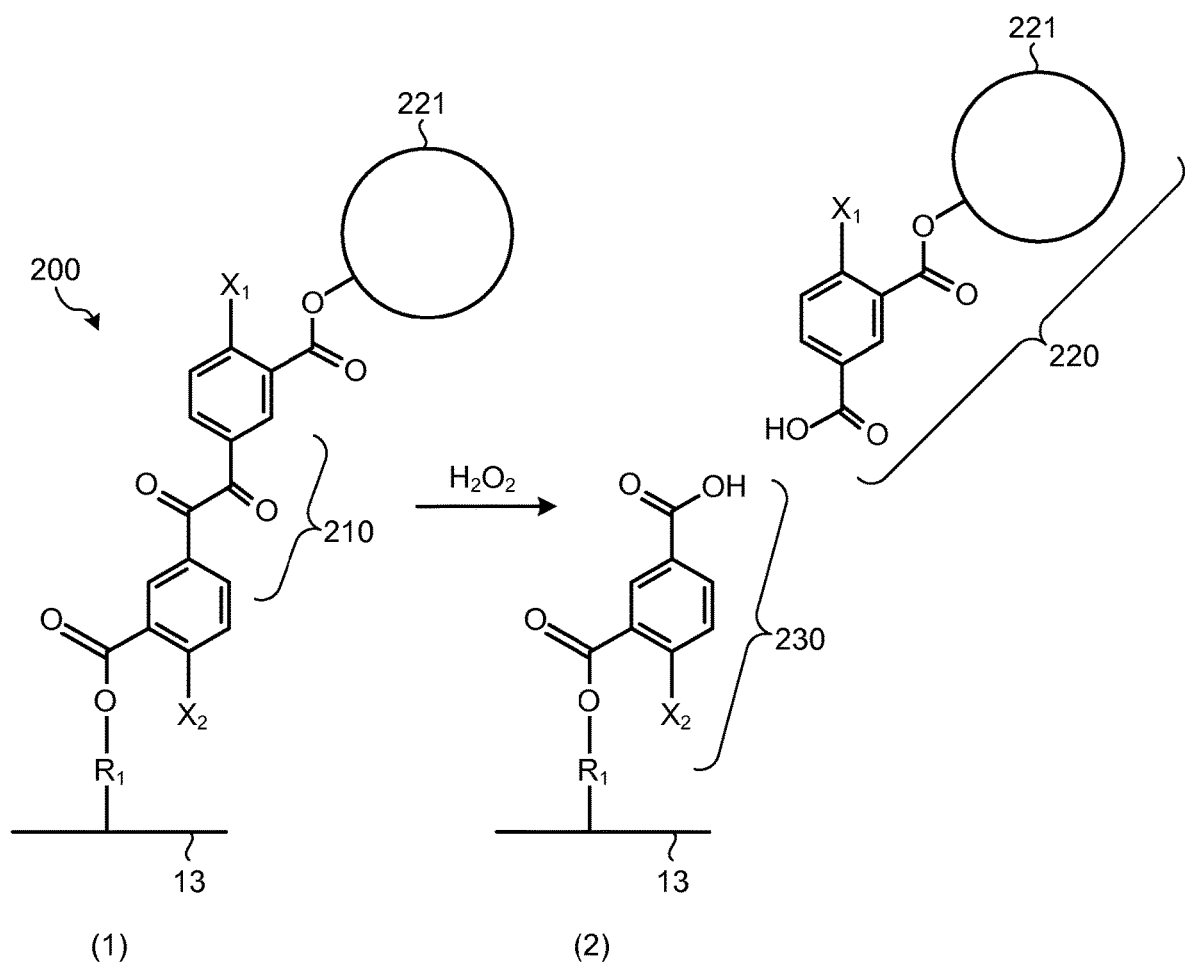
FIG. 15 is an explanatory view of an exemplary sensor according to the embodiment of the present invention.

FIG. 15 is an explanatory view of an exemplary sensor according to the embodiment of the present invention. Instead of a phenylboronic acid ester area, a diketophenyl area is used as another bonding portion in the example in FIG. 15. Similarly to the example illustrated in FIG. 14, nanoparticles 221 are included in the example illustrated in FIG. 15. Herein, in the example illustrated in FIG. 15, the $X_1$ and $X_2$ are each an electron withdrawing group for a benzene ring and are, for example, a nitro group ($NO_2$), a cyano group (CN), a tosyl group (Ts), a mesyl group (MS), an acyl group (-Acyl), a carboxyl group (—COOH), a fluoroalkyl group (a fluorinated alkyl group) (—$C_nF_{2n+1}$), a phenyl group (—$C_6H_5$), a sulfone group (—$SO_3H$), various types of halogen (for example, Cl, Br, or I). Note that, in light of stability, a nitro group and a carboxyl group are preferably used. However, the electron withdrawing group is not limited to the examples. The $X_1$ and $X_2$ may be the same or may be different from each other. In light of synthesis, $X_1=X_2$ may hold. In that case, a nitro group and a carboxyl group are preferable in light of stability.

A method for immobilizing the second substance 200 on the base surface will be described. An arbitrary method may be used as the immobilizing method. For example, using the strong avidity of streptavidin and biotin can immobilize the second substance 200. In the case, for example, the streptavidin is immobilized on the detection unit 13 in advance. More specifically, if the streptavidin is immobilized on the base, a Self-Assembled Monolayer (SAM) made of alkylthiol is formed on the base in advance so as to cover the base surface (for example, Au) as much as possible when the streptavidin is immobilized. The biotin is added to the end portion of the second substance 200 in advance and then a solution including the second substance 200 is produced. Subsequently, making the solution including the second substance 200 in contact with the detection unit 13 immobilizes the second substance 200 on the detection unit 13. Note that the detection unit 13 can subsequently be cleaned with an arbitrary solvent in order to remove the second substance 200 that is not immobilized but remains on the detection unit 13. The solvent for the cleaning is, for example, NaOH. However, the solvent is not limited to NaOH. An arbitrary solvent may be used.

Alternatively, for example, an SAM film is formed on the base surface with a publicly known technique and then is modified with PEG of which terminal is COOH. Subsequently, the base surface is reacted with the second substance 200 including an amine group on its terminal. This can immobilize the second substance 200 on the base surface. Note that, if the second substance 200 including nanoparticles is used, arbitrary nanoparticles are immobilized on a compound of which bond is cleft by the reaction with hydrogen peroxide in the same method for immobilizing the second substance 200 on the base surface and then the compound on which the nanoparticles are immobilized may be used as the second substance 200.

Note that the enzyme to be in contact with the specimen may be attached to an arbitrary place in the sensor in advance. This can make the enzyme in contact with the specimen when the specimen passes through the flow channel. Alternatively, the enzyme to be in contact with the specimen may be dissolved in the specimen before the specimen is sent into the flow channel of the sensor 100. If an enzyme is attached to the sensor in advance, the enzyme is preferably attached not on the base 10 but on the groove. In other words, the sensor includes an enzyme attached to the groove. For example, the enzyme may be attached to the ceiling of the flow channel that faces the detection unit 13 of the base 10, or may be attached to an arbitrary region that forms the internal flow channel in the cover member on which the base 10 is installed.

A hemolyzing agent may additionally be attached to the flow channel. If the specimen is, for example, blood or a solution including blood, attaching a hemolyzing agent to the flow channel can prevent the blood from clotting and thus can surely and easily implement the detection process.

The variations in propagation constant of the SAW are limited to the variations on the extreme surface of the base. Thus, it is not especially necessary to remove the unreacted material that has not been reacted with the target and remains on the upper portion of the base. Merely sending the specimen into the capillary flow channel can selectively detect the effect by the separation of the separation part 220 from the second substance 200.

[Embodiment of Detection Method]

The disclosed detection method includes a preparation process for preparing a sensor 100 including the detection unit 13 on the surface of the base in an embodiment. The second substance 200 is immobilized on the detection unit 13. The second substance 200 includes a bond that is cleft by the reaction with hydrogen peroxide. For example, the sensor 100 configured to detect a first substance to be detected is produced, the sensor 100 is prepared, and the sensor 100 is installed on a detection apparatus.

The detection method includes a contact process for causing the specimen in contact with an enzyme that generates hydrogen peroxide by the reaction with the first substance to be in contact with the detection unit 13 of the sensor 100, in other words, a contact process for causing the specimen in contact with an enzyme that generates hydrogen peroxide by the reaction with the first substance to be in contact with the detection unit 13 of the sensor 100 by introducing the specimen into the detection unit 13. A second substance 200 including a bond that is cleft by the reaction with hydrogen peroxide is immobilized on the detection unit 13. The sensor 100 includes the detection unit 13 on the upper surface of the base 10. In other words, the detection method includes a contact process for causing the specimen in contact with an enzyme that generates hydrogen peroxide by the reaction with the first substance to be in contact with the detection unit 13 of the sensor 100. The sensor 100 includes the detection unit 13 on which a second substance 200 is immobilized. The second substance 200 includes a bonding portion 210 of which bond is cleft by the reaction with hydrogen peroxide. For example, an enzyme is added or mixed into the specimen and this makes the specimen in contact with the enzyme. Then, the specimen may be brought in contact with the base surface of the sensor 100 manually. For example, an enzyme is added or mixed into the specimen and this makes the specimen in contact with the enzyme. Subsequently, the specimen is sent into the flow channel from the inlet 14 of the sensor 100 and then introduced into the detection unit 13 from the inlet 14 through the groove 15. This may cause the specimen to be in contact with the detection unit 13. For example, if an enzyme is attached to the flow channel of the sensor 100 in advance, the specimen is sent from the inlet 14 into the flow channel without change such that the enzyme attached to the flow channel is in contact with the specimen, and then the specimen is introduced from the inlet 14 through the groove 15 to the detection unit 13. This may cause the specimen to be in contact with the detection unit 13. Alternatively, an enzyme may be brought in contact with the specimen and then the specimen may be brought in contact with the base surface of the sensor 100 with another arbitrary method.

The disclosed detection method further includes a detection process for detecting whether the specimen includes the first substance by detecting the cleavage of the bond of the second substance 200. The cleavage is caused by the contact process.

In that case, the variations in state of the base surface include the variations in mass, the variations in electric permittivity, the variations in viscoelasticity, the variations in propagation characteristic, and the variations in resonance frequency. The variations are caused by the fact that the cleavage of the bonding portion of the second substance 200 immobilized on the base surface separates the separation part 220. For example, the bonding portion is cleft and the separation part 220 is separated in the measurement with an SPR apparatus. This varies the mass or electric permittivity of the base surface. This variation causes a variation in SPR angle. In that case, the variations in state of the base surface are the variations in mass, or the variations in electric permittivity caused by the separation of the separation part 220. Detecting the variation in SPR angle detects a variation in state of the base surface. When an SAW sensor is used, the variations in propagation characteristic are caused by the variations in mass, or the variations in viscoelasticity of the base surface. In that case, the variations in state of the base surface are the variations in mass, or the variations in viscoelasticity caused by the separation of the separation part 220. Detecting the variation in propagation characteristic detects a variation in state of the base surface. Alternatively, when a QCM measurement apparatus is used, the variations of resonance frequency are caused by the variations in mass of the base surface. In that case, the variations in the state of the base surface are the variations in mass caused by the separation of the separation part 220. Detecting the variation of resonance frequency detects a variation in state of the base surface.

The variations in state of the base surface are caused by the fact that the separation part 220 of the second substance 200 separates from the detection unit 13. The separation part 220 of the second substance 200 separates when an enzyme generates hydrogen peroxide and the hydrogen peroxide cleaves the bonding portion of the second substance 200. This can easily detect a hydrogen peroxide source.

[Embodiment of Detection System and Detection Apparatus]

The disclosed detection system is for determining whether the specimen includes the first substance in an embodiment. The detection system includes a sensor 100. The sensor 100 includes a detection unit 13 on the surface of the base. A second substance 200 is immobilized on the detection unit 13. The second substance 200 includes a bond that is cleft by the reaction with hydrogen peroxide. The detection system further includes a detection apparatus. In the detection apparatus, the specimen is brought in contact with an enzyme that generates hydrogen peroxide by the reaction with the first substance. Then, the specimen is brought in contact with the detection unit 13 of the sensor 100. Consequently, the detection apparatus detects whether the specimen includes the first substance by detecting the cleavage of the bond of the second substance 200.

In other words, the detection apparatus is for determining whether the specimen includes the first substance. The specimen is brought in contact with an enzyme that generates hydrogen peroxide by the reaction with the first substance. Then, the specimen is brought in contact with the detection unit 13 of the sensor 100. Consequently, the detection apparatus detects whether the specimen includes the first substance by detecting the cleavage of the bond of the second substance 200. The sensor 100 includes the detection unit 13 in which a second substance 200 is immobilized on the surface of the base. The second substance 200 includes a bond that is cleft by the reaction with hydrogen peroxide.

The sensor in that case is the same as the sensor described above. Thus, the description will be omitted. The detection apparatus implements an arbitrary detection process with the sensor described above. The detection apparatus is, for example, an SPR apparatus, an apparatus for controlling an SAW sensor, or a QCM measurement apparatus. The detection apparatus is preferably an apparatus for controlling an SAW sensor. An arbitrary apparatus may be used as the SPR apparatus, the apparatus for controlling an SAW sensor, or the QCM measurement apparatus that works as the disclosed detection apparatus as long as the sensor described above is used for measurement. A publicly known apparatus may be used without change or after an appropriate modification.

The sensor does not detect the first substance directly but detects a variation caused by the separation of the separation part 220 of the second substance 200. In light of the foregoing, the detection apparatus may perform a conversion process for converting the detection result obtained by a signal material or the like into the detection result about the first substance. For example, when the molecular weight of the first substance and the molecular weight of the signal material have been obtained, or when the result that "the separation part 220 is "x" grams [g] (or moles [mol])" is obtained, such a result can be converted into the result that "the first substance is "y" grams [g] (or moles [mol])".

REFERENCE SIGNS LIST

1 FIRST COVER MEMBER
2 SECOND COVER MEMBER
3 DETECTION ELEMENT
4 CONCAVE PORTION FORMING THROUGH-HOLE
5 CONCAVE PORTION
8 NOTCH
10 BASE
11 FIRST IDT ELECTRODE
12 SECOND IDT ELECTRODE
13 DETECTION UNIT
14 INLET
15 GROOVE
100 SENSOR
200 SECOND SUBSTANCE
210 BONDING PORTION
220 SEPARATION PART
221 NANOPARTICLES

The invention claimed is:

1. A sensor configured to determine whether a specimen includes a first substance, the sensor comprising:
a base;
a detection unit comprising a second substance, wherein the second substance is immobilized on the base and includes a bond being cleft by a reaction with a hydrogen peroxide, and wherein the second substance includes a separation part configured to separate from the detection unit by cleavage of the bond;
a flow channel configured to receive the specimen; and
an enzyme configured to generate the hydrogen peroxide by a reaction with the first sub stance,
wherein the base and the detection unit are located inside the flow channel,
wherein the second substance includes a compound selected from the group consisting of a compound represented by formula (1), a compound represented by formula (2), a compound represented by formula (3), and a compound represented by formula (4):

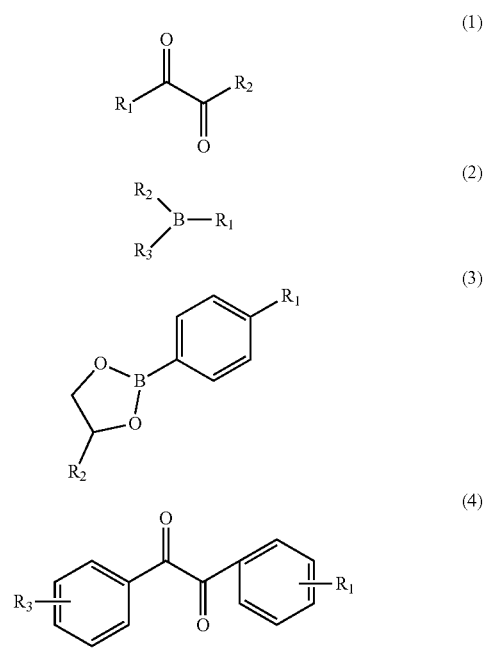

wherein
each of $R_1$ and $R_2$ in any of formulas (1) and (3) is independently an alkyl group, an aryl group, an alkoxy group, or an aryloxy group,
each of $R_1$ and $R_2$ in formula (2) is independently an alkyl group or an aryl group and $R_3$ in formula (2) is an alkyl group, an aryl group, an alkoxy group, or an aryloxy group, or
each of $R_1$, $R_2$, and $R_3$ in formula (2) is independently an alkoxy group or an aryloxy group, and
each of $R_1$ and $R_2$ in formula (4) is independently an alkyl group or an aryl group, and
wherein the detection unit includes a metal film, and the $R_1$, $R_2$ or $R_3$ is bonded to the metal film so that the second substance is immobilized on the detection unit.

2. The sensor according to claim 1, wherein the second substance further includes a nanoparticle at the separation part.

3. The sensor according to claim 1, wherein the second substance includes boronic acid ester including the bond and the separation part includes boronic acid.

4. The sensor according to claim 1, further comprising:
a first cover member on an upper surface of the base; and
a second cover member joined to the first cover member and covering the base, and
wherein at least one of the first cover member and the second cover member comprises an inlet into which the specimen flows, and a groove extending from the inlet at least to the detection unit.

5. The sensor according to claim 4, wherein the first cover member comprises a concave portion accommodating the base on an upper surface of the concave portion, and the second cover member comprises the groove.

6. The sensor according to claim 5, wherein the enzyme is attached to the groove.

7. The sensor according to claim 1, further comprising:
a first InterDigital Transducer (IDT) electrode on a surface of the base, the first IDT electrode configured to generate an acoustic wave propagating toward the detection unit; and
a second IDT electrode on a surface of the base, the second IDT electrode configured to receive the acoustic wave that has passed through the detection unit.

8. The sensor according to claim 7, further comprising:
a first join member joined to the upper surface of the base, the first join member comprising a first oscillation space sealed between the upper surface of the base and the first join member; and
a second join member joined to the upper surface of the base, the second join member comprising a second oscillation space sealed between the upper surface of the base and the second join member,
wherein the first oscillation space is on the first IDT electrode, and the second oscillation space is on the second IDT electrode.

9. A sensor configured to determine whether a specimen includes a first substance, the sensor comprising:
a base;
a detection unit comprising a second substance, wherein the second substance is immobilized on the base and includes a bond being cleft by a reaction with a hydrogen peroxide, and wherein the second substance includes a separation part configured to separate from the detection unit by cleavage of the bond;
an enzyme configured to generate the hydrogen peroxide by a reaction with the first sub stance;
a first InterDigital Transducer (IDT) electrode on a surface of the base, the first IDT electrode being configured to generate an acoustic wave propagating toward the detection unit; and
a second IDT electrode on a surface of the base, the second IDT electrode being configured to receive the acoustic wave that has passed through the detection unit,
wherein the second substance includes a compound selected from the group consisting of a compound represented by formula (1), a compound represented by formula (2), a compound represented by formula (3), and a compound represented by formula (4):

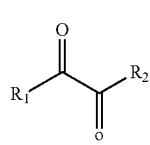

(1)

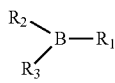

(2)

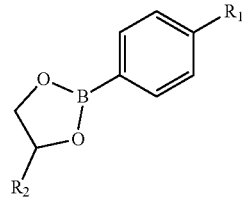

(3)

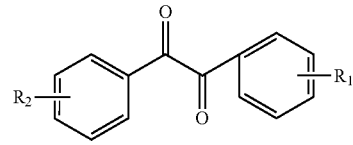

(4)

wherein
each of $R_1$ and $R_2$ in any of formulas (1) and (3) is independently an alkyl group, an aryl group, an alkoxy group, or an aryloxy group,
each of $R_1$ and $R_2$ in formula (2) is independently an alkyl group or an aryl group and $R_3$ in formula (2) is an alkyl group, an aryl group, an alkoxy group, or an aryloxy group, or
each of $R_1$, $R_2$, and $R_3$ in formula (2) is independently an alkoxy group or an aryloxy group, and
each of $R_1$ and $R_2$ in formula (4) is independently an alkyl group or an aryl group, and
wherein the detection unit includes a metal film, and the $R_1$, $R_2$, or $R_3$ is bonded to the metal film so that the second substance is immobilized on the detection unit.

10. The sensor according to claim 9, wherein the second substance further includes a nanoparticle at the separation part.

11. The sensor according to claim 9, wherein the second substance includes boronic acid ester including the bond and the separation part includes boronic acid.

12. The sensor according to claim 9, further comprising:
a first cover member on an upper surface of the base; and
a second cover member joined to the first cover member and covering the base, and
wherein at least one of the first cover member and the second cover member comprises an inlet into which the specimen flows, and
a groove extending from the inlet at least to the detection unit.

13. The sensor according to claim 12, wherein the first cover member comprises a concave portion accommodating the base on an upper surface of the concave portion, and wherein the second cover member comprises the groove.

14. The sensor according to claim 13, wherein the enzyme is attached to the groove.

15. The sensor according to claim 9, further comprising:
a first join member joined to the upper surface of the base, the first join member comprising a first oscillation space sealed between the upper surface of the base and the first join member; and
a second join member joined to the upper surface of the base, the second join member comprising a second oscillation space sealed between the upper surface of the base and the second join member,
wherein the first oscillation space is on the first IDT electrode, and the second oscillation space is on the second IDT electrode.

16. The sensor according to claim 9, wherein the base comprises a piezoelectric base.

\* \* \* \* \*